(12) United States Patent
Beech, Jr.

(10) Patent No.: US 7,799,118 B2
(45) Date of Patent: *Sep. 21, 2010

(54) PRODUCT RECOVERY IN GAS-SOLIDS REACTORS

(75) Inventor: James H. Beech, Jr., Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 766 days.

This patent is subject to a terminal disclaimer.

(21) Appl. No.: 11/729,409

(22) Filed: Mar. 28, 2007

(65) Prior Publication Data

US 2007/0227356 A1    Oct. 4, 2007

Related U.S. Application Data

(60) Provisional application No. 60/788,147, filed on Mar. 31, 2006.

(51) Int. Cl.
C07C 1/00 (2006.01)
B01D 45/00 (2006.01)

(52) U.S. Cl. .......................... 95/267; 95/272; 585/639; 585/640; 585/800; 422/139; 422/141; 422/142; 422/145; 208/146

(58) Field of Classification Search ................. 585/639, 585/800, 640; 422/139, 141, 142, 145; 208/146; 95/267, 272
See application file for complete search history.

(56) References Cited

U.S. PATENT DOCUMENTS

| 4,364,905 A | 12/1982 | Fahrig et al. |
| 4,499,327 A | 2/1985 | Kaiser |
| 4,597,771 A | 7/1986 | Cheng |
| 4,670,993 A | 6/1987 | Dunaway et al. |
| 4,677,242 A | 6/1987 | Kaiser |
| 4,677,243 A | 6/1987 | Kaiser |
| 4,684,375 A | 8/1987 | Morin et al. |
| 4,752,651 A | 6/1988 | Kaiser |
| 4,973,792 A | 11/1990 | Lewis et al. |
| 5,475,182 A | 12/1995 | Janssen |
| 5,531,884 A | 7/1996 | Johnson et al. |
| 5,714,662 A | 2/1998 | Vora et al. |
| 5,744,680 A | 4/1998 | Mulvaney, III et al. |
| 5,817,906 A | 10/1998 | Marker et al. |
| 5,914,433 A | 6/1999 | Marker |
| 5,962,762 A | 10/1999 | Sun et al. |
| 5,990,369 A | 11/1999 | Barger et al. |
| 6,005,150 A | 12/1999 | Vora |
| 6,023,005 A | 2/2000 | Lattner et al. |
| 6,040,264 A | 3/2000 | Sun et al. |

(Continued)

FOREIGN PATENT DOCUMENTS

GB    2 171 718    9/1986

(Continued)

Primary Examiner—Prem C Singh
(74) Attorney, Agent, or Firm—Kevin M. Faulkner; David M. Weisberg

(57) ABSTRACT

A gas-solids reaction system is provided for improving product recovery in a multiple reactor reaction system. The solids of the product gas-solids flows from the multiple reactors are separated out in a separation vessel having a baffled transition zone. Additional product vapor is stripped from the solids as the solids pass through the baffled transition zone. The solids are then returned to the multiple reactors.

30 Claims, 8 Drawing Sheets

U.S. PATENT DOCUMENTS

| | | |
|---|---|---|
| 6,121,503 A | 9/2000 | Janssen et al. |
| 6,121,504 A | 9/2000 | Kuechler et al. |
| 6,166,282 A | 12/2000 | Miller |
| 6,187,983 B1 | 2/2001 | Sun |
| 6,303,839 B1 | 10/2001 | Marker |
| 6,303,841 B1 | 10/2001 | Senetar et al. |
| 6,441,261 B1 | 8/2002 | Kuechler et al. |
| 6,455,747 B1 | 9/2002 | Lattner et al. |
| 6,455,749 B1 | 9/2002 | Vaughn |
| 6,482,998 B1 | 11/2002 | Kuechler et al. |
| 6,482,999 B2 | 11/2002 | Fung et al. |
| 2001/0020119 A1 | 9/2001 | Janssen et al. |
| 2002/0087041 A1 | 7/2002 | Kuechler et al. |
| 2003/0004384 A1 | 1/2003 | Coute et al. |
| 2004/0101449 A1 | 5/2004 | Marchant et al. |
| 2004/0104148 A1 * | 6/2004 | Lomas et al. ............... 208/146 |
| 2007/0232843 A1 | 10/2007 | Beech et al. |

FOREIGN PATENT DOCUMENTS

| | | |
|---|---|---|
| WO | WO 97/36845 | 10/1997 |
| WO | WO 98/02471 | 1/1998 |
| WO | WO 00/41986 | 7/2000 |
| WO | WO 01/62689 | 8/2001 |
| WO | WO 02/32837 | 4/2002 |
| WO | WO 2005/061418 | 7/2005 |

* cited by examiner

Flux values represent flux in standpipes.

PRODUCT RECOVERY IN GAS-SOLIDS REACTORS

CROSS-REFERENCE TO RELATED APPLICATIONS

This application claims priority to application Ser. No. 60/788,147, filed Mar. 31, 2006, which is incorporated by reference.

FIELD OF THE INVENTION

This invention is directed to an apparatus and method for separating gases from solid catalyst particles in a reaction system using a gas-solids flow.

BACKGROUND OF THE INVENTION

Riser reactors provide a convenient reaction system for performing gas-solids reactions. Gas phase reactants can be brought into contact with solid catalyst while inside the riser to convert the reactants into a desired product. Upon exiting the riser, the conversion product is separated from the solids to recover the catalyst.

In reaction systems where only a fraction of the solid catalyst is regenerated during each loop through the system, product vapors generated during one pass through the standpipe or riser reactor can stay with the catalyst during the next pass through the riser reactor. Passing the product vapors through the riser reactor a second time can lead to excess reaction, which can in turn lead to undesirable products and possibly reduce the operating efficiency of the reaction system.

These problems are further compounded in reactor systems having multiple risers. In order to maintain control over the gas-solids reaction, the average state of the solid catalyst in each riser must be the same. To achieve this, a roughly equal amount of regenerated and non-regenerated catalyst should be introduced into each of the multiple risers.

U.S. Pat. No. 4,364,905 describes a single riser FCC reaction system for improving the separation of entrained product vapors from spent catalyst. A stripping gas is conducted through the spent catalyst as it passes through a baffled region. All of the catalyst is then sent to a regenerator.

What is needed is a system and method for improving the separation of gas phase conversion product from catalyst solids. The system and method should be compatible with reaction systems having multiple risers. The system and method should also allow for roughly even distribution of regenerated and non-regenerated catalyst particles into the multiple risers.

SUMMARY OF THE INVENTION

In an embodiment, the invention relates to a method for separating flowing solids comprising:

separating from a gas-solids flow a higher density flow comprising a majority of the solids contained in the gas-solids flow;

conducting the solids from the higher density flow through a transition zone at a transition zone solids flux of at least about $$100 \frac{\text{Kg}}{M^2 \text{sec}}$$

in the presence of a displacing gas flowing counter-currently with respect to average solids flow; and then conducting the displaced solids away from the transition zone.

In a related embodiment, the solids comprise catalyst particles containing molecular sieve with hydrocarbon and/or oxygenated hydrocarbon thereon or therein. Optionally, the hydrocarbon and/or oxygenated hydrocarbon are displaced from the catalyst particles in the transition zone at a displacing efficiency of at least 50%. Optionally, the catalyst particles contain molecular sieve, preferably SAPO molecular sieve, more preferably SAPO 18 and SAPO 34 molecular sieve, and still more preferably SAPO 34 molecular sieve.

In an embodiment, the transition zone comprises
(a) a solids inlet,
(b) a solids outlet having an area A, and
(c) a displacing gas inlet, located a vertical distance D from the solids outlet wherein D and A are related by the function $D = KA^{0.5}$ with K ranging from about 0.3 to about 1.5, preferably from about 0.8 to about 1.1. In a related embodiment, the transition zone comprises at least one baffle layer, and wherein the displacing gas inlets are either (i) proximate to the baffle layer closest to the solids outlet or (ii) between the solids outlet and the baffle layer closest to the solids outlet.

In a preferred embodiment,
(i) the catalyst particles have an average flux through the transition zone ranging from $$125 \frac{\text{Kg}}{M^2 \text{sec}} \text{ to } 488 \frac{\text{Kg}}{M^2 \text{sec}},$$

(ii) the catalyst particles have an average catalyst residence time in the transition zones ranging from 5 seconds to 10 minutes, and
(iii) the catalyst particles in the transition zone have an average catalyst density gradient of 525 kg/m³-m or less,
(iv) at least 95 wt. % of the catalyst particles in the transition zone have an average particles size of 125 micrometers or less based on the total weight of catalyst particles in the transition zone; and
(iv) D is at least 250 mm and A is at least $2.7 \times 10^4$ square millimeters.

In an embodiment, the catalyst is conducted away from the transition zone through the solids outlet and into a standpipe having a standpipe cross-sectional area no greater than A. While not required, the transition zone can comprise a plurality of solids outlets with each having a cross sectional area equal to A. The catalyst is conducted away from the transition zone through the plurality solids outlets into a plurality of standpipes. Each of the standpipes has an upstream end directly connected to one of the transition zone's solids outlets. Optionally, each standpipe is of even cross sectional area with the transition zone outlet to which the standpipe is connected, i.e., both the transition zone solids outlet and the standpipe to which it connects have cross sectional areas equal to A. Preferably, the standpipes and the transition zone outlets have a circular cross section.

In yet another embodiment, the invention relates to a method for separating flowing catalyst particles comprising:

separating from a gas-catalyst flow a higher density flow comprising a majority of the catalyst particles contained in the gas-catalyst flow; conducting the catalyst particles from the higher density flow through a transition zone at a transition zone catalyst flux ranging from $$125 \frac{\text{Kg}}{M^2 \text{sec}} \text{ to } 488 \frac{\text{Kg}}{M^2 \text{sec}}$$

in the presence of steam, with the steam flowing counter-currently with respect to average catalyst particle flow at a gas superficial velocity of at least about 0.09 meters per second, with the catalyst particles in the transition zone have an average catalyst density gradient of 525 kg/m$^3$-m or less; with the catalyst particles having an average catalyst residence time in the transition zones ranging from 5 seconds to 10 minutes, with at least 95 wt. % of the catalyst particles in the transition zone having an average particles size of 125 micrometers or less based on the total weight of catalyst particles in the transition zone; and then conducting the displaced catalyst particles away from the transition zone; wherein the transition zone comprises
   (a) a solids inlet for conducting catalyst into the transition zone,
   (b) a solids outlet having a cross sectional area A for conducting catalyst away from the transition zone,
   (c) a baffle layer located between the solids inlet and the solids outlet, and
   (d) a displacing gas inlet, located a distance D from the solids outlet and either (i) proximate to the baffle layer or (ii) between the solids outlet and the baffle layer; wherein D and A are related by the function D=KA$^{0.5}$ wherein K ranges from about 0.3 to 1.5 (preferably 0.8 to 1.1); D is at least 250 mm; and A is at least 2.7×10$^4$ square millimeters.

In still another embodiment, the invention relates to a method for separating solids from a gas-solids flow comprising:

producing a gas-solids flow by performing an oxygenate to olefin conversion reaction in a riser reactor;

separating from the gas-solids flow a higher density flow comprising a majority of the solids contained in the gas-solids flow;

conducting the solids from each higher density flow to a transition zone;

conducting the solids from the higher density flow through a transition zone at a transition zone solids flux of at least $$100 \frac{\text{Kg}}{M^2 \text{sec}}$$

in the presence of a displacing gas flowing counter-currently with respect to average solids flow; and then conducting the solids away from the transition zone to the olefin conversion reactor; the transition zone comprising
   (a) a solids inlet,
   (b) a solids outlet having an area A,
   (c) a baffle layer located between the solids inlet and the solids outlet,
   (d) a displacing gas inlet, located a distance D from the solids outlet and either (i) proximate to the baffle layer or (ii) between the solids outlet and the baffle layer; wherein D and A are related by the function D=KA$^{0.5}$ with K ranging from about 0.8 to 1.5.

Optionally, the transition zone comprises a plurality of baffle layers, wherein the displacing gas inlets are either (i) proximate to the baffle layer closest to the solids outlet or (ii) between the solids outlet and the baffle layer closest to the solids outlet. Optionally, the transition zone comprises at least one pair of baffle layers, wherein an orientation of one layer of the pair of baffle layers is rotated by 90 degrees relative to the second layer of the pair of baffle layers. Optionally, a superficial velocity of the displacing gas within the transition zone is 0.03 m/sec or greater.

In a related embodiment, (i) the solids comprise catalyst particles containing molecular sieve with hydrocarbon and/or oxygenated hydrocarbon thereon or therein, and (ii) the hydrocarbon and/or oxygenated hydrocarbon is stripped from the catalyst particles in the transition zone at a stripping efficiency of at least 50%. Optionally, the displacing gas is steam, and the steam has a gas superficial velocity in the transition zone of at least 0.09 meters per second.

Within the transition zone
(i) the average catalyst flux optionally ranges from $$125 \frac{\text{Kg}}{M^2 \text{sec}} \text{ to } 488 \frac{\text{Kg}}{M^2 \text{sec}},$$

(ii) the average catalyst residence time optionally ranges from 5 seconds to 10 minutes, and
(iii) the average catalyst density gradient is optionally 525 kg/m$^3$-m or less, and
(iv) D is optionally at least 250 mm and A is at least 2.7×10$^4$ square millimeters.

In a related embodiment, the catalyst is conducted away from the transition zone through the solids outlet and into the upstream end of a standpipe having a standpipe cross-sectional area no greater than A, and then from the downstream end of the standpipe to the olefin conversion reactor, i.e., the riser reactor. Optionally, the transition zone comprises a plurality of solids outlets with each having a cross sectional area A. The catalyst is conducted away from the transition zone through the plurality solids outlets into a plurality of standpipes to the olefin conversion reactor, the standpipes each having (i) an upstream end directly connected to one of the transition zone's solids outlets with the standpipe being of even cross-sectional area with the connected transition zone outlet (i.e., both equal to A) and (ii) a downstream end. In a related embodiment, the olefin conversion reactor comprises a plurality of riser reactors, where the catalyst is conducted from the downstream end of each standpipe into at least one riser of the riser reactor.

Optionally, at least a portion of the catalyst in the transition zone is in a fluidized bed, the fluidized bed having a density gradient of 53 kg/m$^3$-m or less, and wherein there is a volume fraction of bubbles at the catalyst outlet of at least 0.00005.

In another embodiment, the invention relates to a method for making olefins, comprising contacting a feed containing at least one oxygenate with a SAPO-containing catalyst in a riser reactor, separating the catalyst particles from the olefins and conducting at least a portion of the catalyst to a transition zone having a catalyst flux of at least $$100 \frac{Kg}{M^2 sec}$$

in the presence of a displacing gas flowing counter-currently with respect M sec to average catalyst flow, displacing at least some of the oxygenate and/or olefin from the catalyst in the transition zone, and then conducting at least a portion of the displaced catalyst to the riser reactor.

Optionally, the transition zone comprises
(a) a catalyst inlet,
(b) a catalyst outlet having an area A, and
(c) a displacing gas inlet, located a vertical distance D from the catalyst outlet wherein D and A are related by the function $D=KA^{0.5}$ with K ranging from about 0.3 to 1.5.

Optionally, the catalyst is in the form of catalyst particles containing SAPO molecular sieve, and
(i) the catalyst particles have an average flux through the transition zone ranging from $$125 \frac{Kg}{M^2 sec} \text{ to } 488 \frac{Kg}{M^2 sec},$$

(ii) the catalyst particles have an average catalyst residence time in the transition zones ranging from 5 seconds to 10 minutes, and
(iii) the catalyst particles in the transition zone have an average catalyst density gradient of 525 kg/m³-m or less,
(iv) at least 95 wt. % of the catalyst particles in the transition zone have an average particles size of 125 micrometers or less based on the total weight of catalyst particles in the transition zone;
(iv) D is at least 250 mm and A is at least $2.7 \times 10^4$ square millimeters, (v) K ranges from about 0.8 to about 1.1; and
(v) the displacing gas is steam.

In a related embodiment, the transition zone comprises a plurality of catalyst outlets, each of the catalyst outlets having a cross sectional area equal to A, and wherein at least a portion of the catalyst is conducted away from the transition zone through each of the plurality catalyst outlets into a plurality of standpipes and then to the riser reactor, each of the standpipes having the same cross sectional area as the catalyst outlet to which it connects, and wherein the catalyst flux in the standpipes ranges from about 488 Kg/m² sec to about 1700 Kg/m² sec.

DETAILED DESCRIPTION OF THE INVENTION

Figure 1:
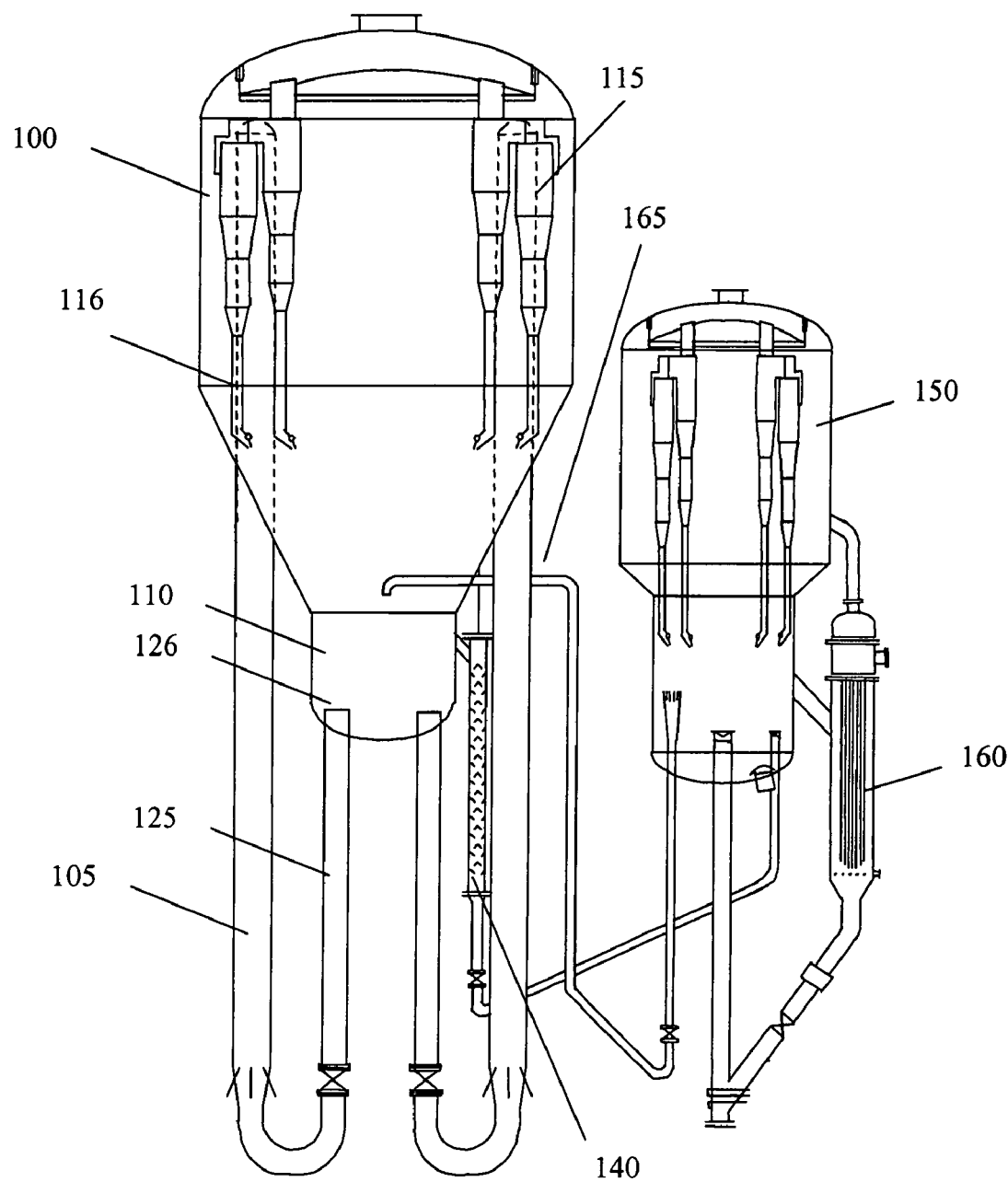
FIG. 1 schematically shows a reaction system according to an embodiment of the invention.

The invention relates in part to the discovery of a relationship between the location of the displacing gas inlet in a transition zone and the maximum stable flux for solids in gas-solids flow in one or more standpipes connected to the downstream end of the displacement zone. For a stable solids flux in the range of about 100 lb/ft²*sec (about 488 kg/m²*sec) to about 350 lb/ft²*sec (about 1710 kg/m²*sec), preferably 200 lb/ft²*sec to about 300 lb/ft²*sec (about 976 kg/m²*sec to about 1460 kg/m²*sec), in one or more standpipes of cross sectional area A, the displacing gas inlet into the transition zone should be located a distance D above the connection between the downstream end of the transition zone where it connects to the upstream end of the standpipe. The value for D can be determined from the relationship $D=K*A^{0.5}$ where K ranges from about 0.3 to about 1.5, preferably about 0.8 to about 1.1.

The invention also relates in part to the discovery that in an oxygenate-to-olefin reaction system, a superficial velocity of the displacing gas in the transition zone of 0.3 ft/sec (0.09 m/sec) and above results in improved displacement (e.g., stripping) efficiency, improved prime olefin selectivity, and diminished coke selectivity. It has also been discovered that in an oxygenate-to-olefin reaction system, transition zone displacement efficiency can be maintained even at relatively high catalyst flux (in the transition zone) of about 100 Kg/m² sec and higher, or about 125 Kg/m² sec and higher, or about 150 Kg/m² sec and higher. In other words, the transition zone of an oxygenate-to-olefin reaction system can efficiently operate at a significantly higher transition zone flux than other fluidized-catalyst reaction systems (e.g., the fluidized catalytic cracking of a gas oil), which would exhibit a significant decrease in stripping efficiency at a flux of about 95 Kg/m² sec and above.

While it should be understood that it is not limited thereto, a fluidized-catalyst reaction system is a convenient context for describing embodiments of the invention. Accordingly, aspects of invention will be first described in embodiments that relate to fluidized-solids reactions, and in particular to fluidized-solids reaction systems using oxygenate feeds to produce olefins.

Flow of Solid Catalyst in a Fluidized-Catalyst Reaction System

In a fluidized-catalyst reaction system, solid particles having activity for catalyzing the desired reaction are introduced one or more risers. The desired feedstock is conducted into the riser at a point downstream of the catalyst inlet. The feedstock reacts with the catalyst to make the desired product, and catalyst, unreacted feedstock, desired product, and any byproducts formed flow up the riser (i.e., in the downstream direction) to the downstream end of the riser. In an embodiment, the riser can have a diameter of at least about 1 meter, or at least about 1.5 meters, or at least about 2 meters, or at least about 3 meters, or at least about 4 meters, or at least about 5 meters, or at least about 6 meters. In another embodiment, the riser can have a diameter of about 9 meters or less. The diameter of the riser can vary over the length of the riser. For the purposes of this invention, the diameter of the riser refers to the diameter of the riser at the location where the riser is joined to the termination device.

The downstream end of the riser is connected to a separation zone comprising a termination device and one or more gas-solids separators (e.g., cyclone separators) for separating solid particles such as catalyst and catalyst fines from the gas-solids flow exiting the riser. The riser and termination device can be coupled in any convenient manner.

As the gas-solids flow passes through the separation devices, the flow is separated into a higher density (primarily solids) flow and lower density (primarily gas) flow by each device. For example, in an embodiment where the separation devices are cyclone separator stages, each stage produces a higher density flow that exits the cyclone separator stage through a dipleg. The lower density flow is either passed into the next cyclone separator stage, or after the final stage the lower density flow is passed out of the separation vessel. Because the cyclone separator stages are not perfectly efficient, some product gas will be entrained with the higher density flow as it exits through the dipleg.

After exiting the dipleg, the solid catalyst from a higher density flow (and any entrained product vapor) is received into a transition zone in the separation vessel. In an embodiment, the transition zone contains a fluidized bed of the catalyst solids. Catalyst is conducted from the fluidized catalyst bed in the transition zone downward toward the downstream end of the transition zone where the transition zone terminates in one or more standpipes. As is the case with the transition zone, the catalyst in the standpipe is preferably in the form of fluidized solids. The downstream opening of the transition zone is connected to the upstream opening of one or more standpipes. Consequently, catalyst flows from the transition zone downstream into the upstream opening of the standpipe(s), and then flows downward in the standpipe to the downstream opening of the standpipe which is connected to the upstream opening of the riser (i.e., the riser's catalyst inlet). Once the catalyst has been returned to the riser, it becomes available to continue the gas-solids reaction with the feedstock. In a preferred embodiment, the process is operated continuously.

Preferably, a portion of the solid catalyst from the catalyst bed and/or the higher density flows exiting the cyclone separator stages can be diverted into a regenerator. The location in the transition zone for withdrawing catalyst for diversion to the regenerator can be at any convenient height of the catalyst bed subsisting in the transition zone. When catalyst is returned from the regenerator, the regenerated catalyst can be distributed e.g., at the top of the catalyst bed. The distribution method for returning the catalyst to the top of the catalyst bed can be any convenient catalyst distribution method, including conventional methods.

Like the riser, the standpipe is preferably but not necessarily in the shape of a hollow cylinder, i.e., a tube having a circular cross-sectional area, but this is not required. As in the case of the riser, tubing of any convenient cross-sectional geometry can be used. The standpipe can have a constant cross-sectional area over its length, or the diameter can vary along the standpipe. In an embodiment, the standpipe entry (i.e., the upstream and/or downstream opening of the standpipe) has a circular cross sectional area with a diameter of at least about 0.5 meters, or at least about 0.75 meters, or at least about 1 meter. In another embodiment, the standpipe entry can have a diameter of about 2 meters or less. When the standpipe has a non-constant cross sectional area, the cross sectional area is determined at the location where the solid catalyst enters the standpipe from a downstream opening of the transition zone. While there is generally a one to one correspondence between the number of standpipes and the number of risers, this is not required. In an embodiment, a single standpipe can provide catalyst to a plurality of risers. In another embodiment, a single riser can receive catalyst from a plurality of standpipes. In yet another embodiment, the system comprises at least one standpipe providing catalyst to a plurality of risers and at least one riser receiving catalyst from a plurality of standpipes.

FIG. 1 schematically shows an embodiment of a reaction system suitable for use in the invention. A plurality of riser reactors 105 are provided for performing a gas-solids reaction. The tops of risers 105 (and the riser termination devices) are not shown as they are contained within separation vessel 100. The downstream riser opening (located near the top of each riser) are coupled with cyclone separator stages 115. During operation, solids separated by the cyclone separator stages 115 pass out of the diplegs 116 toward transition zone 110 of separation vessel 100. As shown, the upstream opening of the transition zone is connected to the downstream portion of the separation vessel by a conical section. Preferably, a catalyst bed will be formed by the catalyst in the bottom region of the transition zone. Catalyst from this catalyst bed feeds catalyst to downstream openings of the transition zone and into the upstream openings 126 of the standpipes 125. A portion of the catalyst in the catalyst bed can be diverted to regenerator 150 via the conduit containing catalyst stripper 140. Regenerator 150 is optionally provided with a catalyst cooler 160. Regenerated catalyst can be returned via conduit 165. In the embodiment shown in FIG. 1, regenerated catalyst is returned to the top of the transition zone to join the catalyst exiting the cyclone diplegs. More generally, regenerated catalyst can be distributed at the top of the catalyst bed in the transition zone by any convenient catalyst distribution means, including conventional catalyst distribution means.

Transition Zone

In fluidized-catalyst reaction systems using molecular sieve catalyst, a significant portion of the desired reaction product made in the riser can adhere to the catalyst. For some molecular sieve catalysts such as those containing SAPO molecular sieve e.g., SAPO 34, about 2 wt. % to about 5 wt. % or more of the desired product can be adhered to the catalyst. As the catalyst continuously traverses the reaction system, the portion of the desired product adhered to the catalyst can continue to react. This extended exposure of gas phase product to the solid catalyst can result in additional coke formation and the production of other undesirable (e.g., over-reaction) products, such as saturated hydrocarbons. In addition to detrimentally affecting desired product yield, coke and/or other over-reaction products adhered on the catalyst can modify the reactivity of the catalyst, leading to undesirable changes in the catalytic conversion of the feed to the desired products. Thus, separating out some or all of this product gas and preventing it from entering the riser will not only increase the amount of product recovered from the reaction system, but will also reduce the amount of undesired products that could lead to degradation of the system performance.

The transition zone is configured to remove adhered product from the catalyst in order to ameliorate the aforementioned difficulties. When a plurality of standpipes is used, the system provides for approximately equivalent distribution of catalyst among the standpipes so that an approximately equal amount of catalyst can be conducted into each riser, particularly at high transition zone catalyst fluxes of about 100 $Kg/m^2$ sec and above, or about 125 $Kg/m^2$ sec and above, or about 150 $Kg/m^2$ sec and above; and high standpipe catalyst fluxes of about 980 $Kg/m^2$ sec to about 1460 $Kg/m^2$ sec. In an embodiment, improved separation of product gases from solid catalyst can be achieved by passing the catalyst through a transition zone containing a series of baffle structures and one or more gas delivery inlets, such as one or more gas spargers. The sparger or spargers are configured to introduce a displacing gas which moves countercurrent with respect to catalyst flow. In other words, a portion of the displacing gas flows out the upstream (with respect to catalyst flow) end of transition zone 110 into vessel 100. The displacing gas assists in removing desired product adhered to the catalyst and in the transport of desired product away from the transition zone into separation vessel 100.

When a regenerator is used, catalyst from the regenerator can be returned to the top of the transition zone, to allow time for the regenerated and non-regenerated catalyst to mix and/or distribute evenly. At the bottom (downstream end with respect to catalyst flow) of the transition zone, the catalyst passes into the standpipe entry for each riser.

In various embodiments, the structures in the transition zone facilitate improved separation of product gases from the solid catalyst. As the solid catalyst travels down through the baffles, the solid catalyst is contacted with the displacing gas. In an embodiment, these inlets can be positioned just below the last (most downstream with respect to catalyst flow) tier of baffles. The gas introduced by the gas inlets can be steam, nitrogen, or another gas that will not react significantly with the solid catalyst or the product.

When used, the baffles can be of any geometry capable of impeding the flow of catalyst through the transition zone. For example, the baffles can be a series of bars or other solid structures arranged parallel to each other that span the interior of the transition zone at a given height in the transition zone. The baffles can be partially solid, i.e., they can have solid regions where no catalyst can pass and open regions where catalyst can freely pass. In other embodiments, the baffles can be sheds, gratings, packing, or any other suitable solid structures. In an embodiment, multiple levels of baffles can be used such as a series of sheds, gratings, or other solid structures. When the baffles are arranged in levels or tiers, the solid structure portions of the baffles in each level can be aligned, or the solid structure portions can be offset so that the openings in one level of baffles align with the solid structure portions of the subsequent level. Other arrangements, such as aligning the solid structure portions of baffle levels perpendicular to each other, or rotating the baffles at another angle, can also be selected. In an embodiment, at least 2 levels of baffle structures can be used, or at least 4, or at least 5, or at least 6, or at least 8. In another embodiment, 10 or fewer levels of baffle structures can be used. In still another embodiment, baffles can be arranged in pairs of levels. Within a pair of baffle levels, the axes of baffles in one level can be aligned with the axes of the baffles in the second level. For example, the baffles in one level can be rotated 90 degrees relative to the second level. Alternatively, the baffles in one level can be offset to align openings in one level with solid portions in the second level.

In an embodiment, the solid structures used to form the baffles can have various geometries. For example, the solid structures can have a rectangular profile, a triangular profile, or any other convenient solid geometry. In another embodiment, the baffles can be in the form of "sheds." The sheds can have a "v-shaped" profile that is inverted so that the catalyst approaches the point of the "v" as the catalyst moves through the transition zone. Preferably, the sheds can also include a small vertical surface at the bottom edges of the inverted v-shape. Various orientations can be selected for the sheds. All of the sheds can be aligned, or each successive level of sheds can be oriented at an offset, such as a 90 degree offset. Similarly, the positioning of the sheds in each level can offset, as noted above. In still another embodiment, a commercially available packing material such as Koch Glitsch FCC stripper packing can be used as a baffle material.

In an embodiment, at least a portion of the baffles in at least one tier are perforated or otherwise have openings to allow gas to pass through the baffle structure. For example, the baffles can have a series of about 1 cm to about 3 cm diameter holes spaced evenly along the length of the baffle, or in more than one row spread evenly along the length of the baffle. The holes can be separated by at least about 2 cm, or at least about 3 cm, or at least about 4 cm. Alternatively, the holes can be about 6 cm or less apart.

In still another embodiment, one or more displacing-gas spargers or other displacing-gas inlets can be provided in the transition zone. In a related embodiment, the displacing-gas inlets can be located below the lowest level of baffles within the transition zone. Alternatively, the displacing-gas inlet structures can serve as the lowest level of baffles within the transition zone. In a related embodiment, the displacing-gas s inlet (or sparger) structure is the sole baffle in the transition zone.

Figure 2A:
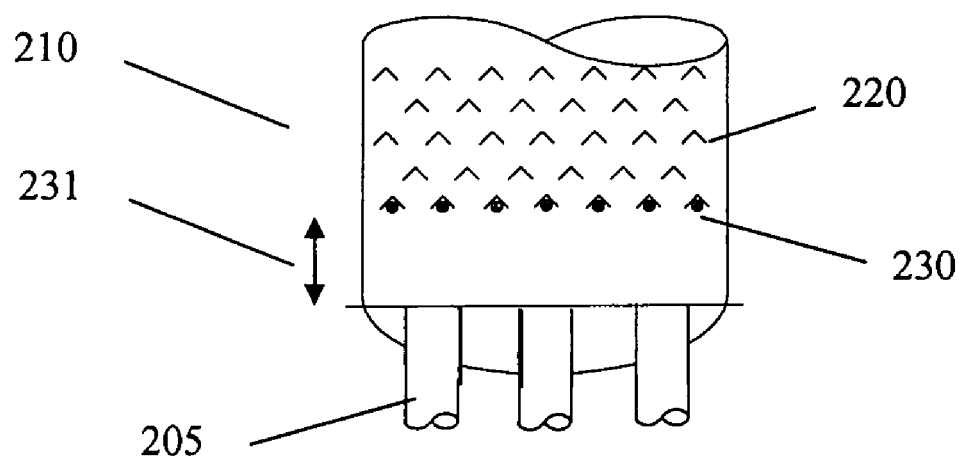
FIGS. 2A and 2B schematically show a portion of a reaction system according to an embodiment of the invention.
Figure 2B:
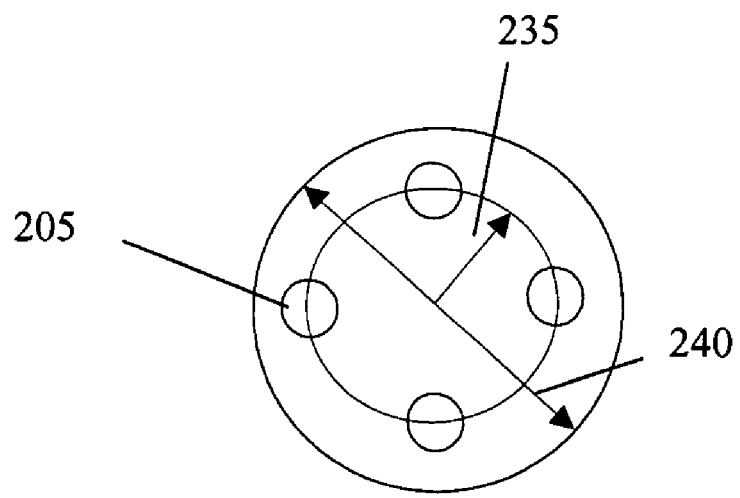

FIGS. 2A and 2B schematically show an example of a transition zone 210 in a separation vessel according to an embodiment of the invention. FIG. 2A shows a side view of the transition zone 210. In the embodiment shown in FIG. 2A, 5 levels of baffles 220 are used. Each level of baffles is oriented perpendicular to the plane of the drawing. The baffle structures in successive levels are offset from one another, so that an open space in one level is positioned above a baffle structure in the next level. In the embodiment depicted, the baffle structures are inverted v-shaped structures. Preferably, a vertical piece can be attached to the bottom edge of each v-shaped structure. A series of gas spargers 230 is also located underneath the lowest level of baffle structures 220. Preferably, each of the baffle structures 220 is perforated to allow gas to pass through the structures. The gas spargers 230 are separated from the entry locations for the standpipes 205 by a distance 231.

Figure 4:
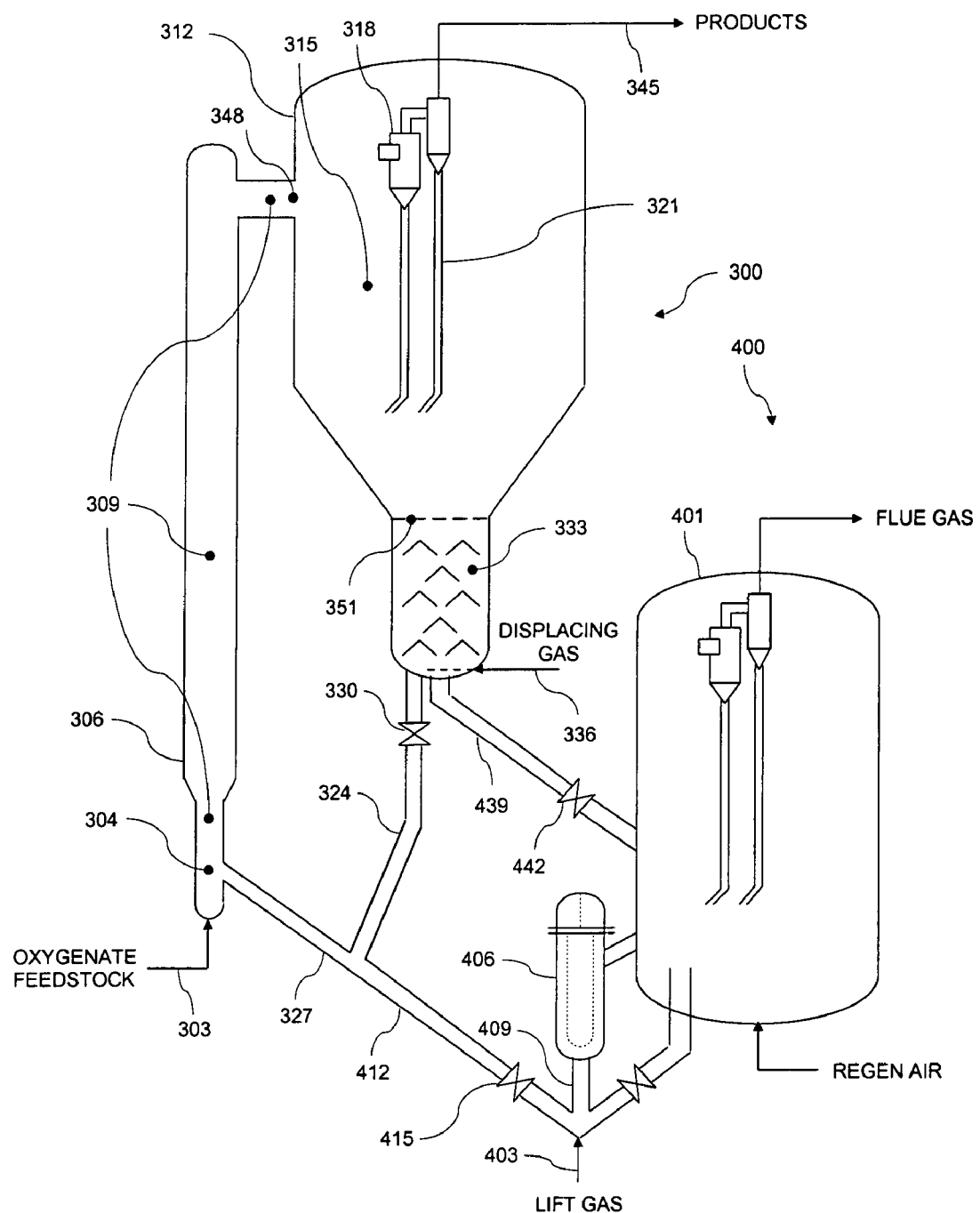
FIG. 4 schematically shows an apparatus according to an embodiment of the invention.

FIG. 2B depicts a top-down cross-sectional view of the transition zone. As shown in FIG. 2B, 4 standpipes 205 are connected to the separation vessel that includes transition zone 210. FIG. 2B also shows a comparison between a radius 235 from the center of the transition zone 210 to the center of the standpipes 205, and the overall diameter 240 of the transition zone. In this example, the ratio of the radius to the center of the standpipes and the diameter of the transition zone is 0.32. In other embodiments, this ratio can be at least about 0.2, or at least about 0.25, or at least about 0.3. In still other embodiments, this ratio can be about 0.4 or less, or about 0.35 or less.

To facilitate the flow of solid catalyst through the reaction system, the bottom row of baffles and/or the gas delivery inlets are separated from the riser feed standpipe entrances by a minimum distance. The separation distance is dependent on the cross sectional area of the standpipes at the entry location (i.e., where the upstream end of the standpipe connects to the downstream end of the transition zone) and the desired solid catalyst flux through the standpipes and reaction system. Larger distances between the riser standpipe entry and the gas delivery inlets and/or bottom row of baffles will allow for higher catalyst flux through the standpipes and reaction system (while maintaining catalyst fluidization in the standpipe) for a given standpipe cross sectional area. Larger cross sectional areas for the standpipes tend to reduce the maximum stable catalyst flux for a given separation distance. These effects, illustrated in FIG. 3, result from the amount of de-aeration taking place in the transition zone, with a longer separation distance providing more de-aeration and allowing higher flux. However, too much de-aeration, such as would occur with too large of a separation distance, can lead to complete defluidization of the catalyst and a sudden loss of catalyst flow. Consequently, enough gas must be present with the catalyst so as to maintain catalyst fluidization in the standpipe. In other words, as solid catalyst flows below the gas inlet (such as a gas sparger), the total amount of gas in contact with the solid catalyst will be gradually reduced. If the quantity of gas is too low, the solid catalyst could lose some or all of its fluidization properties, resulting in poor flow behavior for the catalyst in the bed below the gas inlet. To avoid this, the distance between the gas spargers and the entry locations to the standpipes should be close enough so that the solid catalyst retains a desired level of fluidization. In order to quantify the level of fluidization of a catalyst bed, the "defluidization" of the catalyst can be expressed as the volume fraction of gas bubbles in the catalyst relative to the total volume of the gas/catalyst mixture. In an embodiment, the defluidization of the solid catalyst at the entry location for the standpipes can be about 0.00005 or more, or about 0.0001 or more, or about 0.0002 or more.

Figure 3:
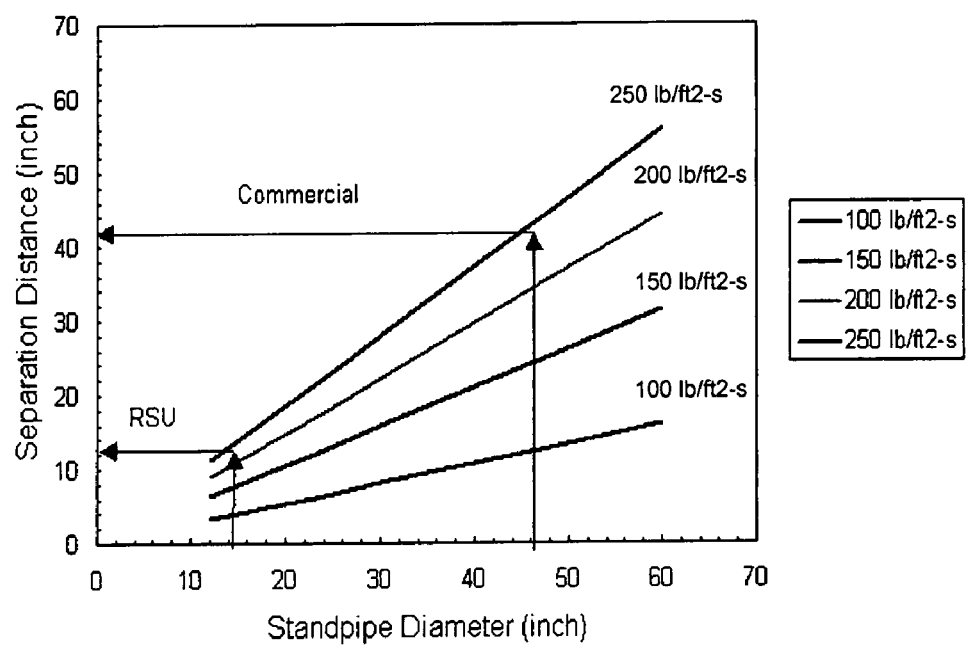
FIG. 3 shows expected performance characteristics for an apparatus according to an embodiment of the invention.

The catalyst flux relationships shown in FIG. 3 are characteristic of a transition zone terminating in a single standpipe or in a plurality of standpipes. When the transition zone of the separation vessel is similar to the transition zone shown in FIGS. 2A and 2B, the data shown in FIG. 3 corresponds to a maximum stable flux for solids in the gas solids flow in the plurality of standpipes. As shown in FIG. 3, the maximum stable flux increases as the distance (height) increases between the gas inlets (spargers) and the standpipe entry locations. The lowest catalyst flux shown is 100 lb/ft$^2$*sec (488 kg/m$^2$*sec), which corresponds to a typical minimum desired catalyst flux within the standpipe. At a typical commercial standpipe diameter of 46 inches (117 cm), a separation of roughly 10 inches (25 cm) would be required between the bottom of the gas spargers and the entry point for the catalyst into the standpipes. At the same standpipe diameter, maintaining a desirable commercial value of about 250 lb/ft$^2$*sec (1221 kg/m$^2$*sec) requires a separation distance of about 40 inches (102 cm) between the gas spargers and the standpipes. Since the standpipe can have a non-circular cross-sectional area, FIG. 3 can also be expressed with the standpipe cross-sectional area on the X axis, instead of standpipe diameter which assumes a circular cross section. Accordingly, the relationship of FIG. 3 can be expressed as D=KA$^{0.5}$ where K ranges from about 0.3 to 1.5; D is at least 250 mm; and A is at least 2.7×10$^4$ square millimeters to provide a stable fluidized catalyst flux in the standpipe ranging from about 100 lb/ft$^2$*sec to about 350 lb/ft$^2$*sec (about 488 Kg/m$^2$ sec to about 1710 Kg/m$^2$ sec). Standpipe fluidization generally becomes unsustainable at catalyst fluxes of about 1710 Kg/m$^2$ sec to about 1950 Kg/m$^2$ sec, and above.

In particular embodiments, the distance between the displacing-gas spargers (or other displacing-gas inlets) and the entry locations for the standpipes is at least about 10 inches (25 cm), or at least about 50 cm, or at least about 75 cm, or at least about 100 cm. In other embodiments, the distance between the gas spargers (or other gas inlets) and the entry locations for the standpipes is about 300 cm or less.

In an embodiment, transition zone is in the form of a fluidized bed. In a preferred embodiment, the absolute catalyst density within the transition zone ranges from about 50% to about 90% of the catalyst's minimum fluidization density. In an embodiment, the density of fluidized material within the transition zone can be at least about 400 Kg/m$^3$, or at least about 480 Kg/m$^3$. In another embodiment, the density of the fluidized material in the transition zone can be about 720 Kg/m$^3$ or less, or about 640 Kg/m$^3$ or less. It is believed that a catalyst density gradient greater than about 5 lb/ft$^3$-ft (266 kg/m$^3$*m) will result in reduced value for the maximum catalyst flux that can flow through a reaction system. Thus, in various embodiments the reaction system can be operated to have a density gradient of about 10 lb/ft$^3$-ft (525 kg/m$^3$-m) or less, or about 5 lb/ft$^3$-ft (263 kg/m$^3$-m) or less, or about 4 lb/ft$^3$-ft (210 kg/m$^3$-m) or less, or about 3 lb/ft$^3$-ft (158 kg/m$^3$-m) or less, or about 1 lb/ft$^3$-ft (53 kg/m$^3$-m) or less.

The catalyst flux within the transition zone can also be characterized. In an embodiment, the catalyst flux within the transition zone ranges from about 10 lb/ft$^2$*sec (48.8 kg/m$^2$*sec) to about 50 lb/ft$^2$*sec (244 kg/m$^2$*sec). In another embodiment, the catalyst flux ranges from about 25 lb/ft$^2$*sec (122 kg/m$^2$*sec) to about 50 lb/ft$^2$*sec (244 kg/m$^2$*sec). In another embodiment, the catalyst flux ranges from $$125 \frac{Kg}{M^2 sec} \text{ to } 488 \frac{Kg}{M^2 sec}.$$

In another embodiment, the catalyst flux is at least about 100 kg/m$^2$*sec or at least about 125 kg/m$^2$*sec, or at least about 130 kg/m$^2$*sec.

In an embodiment, the residence time for catalyst in the transition zone can be about 60 minutes or less, or about 10 minutes or less, or about 1 minute or less. In another embodiment, the residence time can be at least about 5 seconds, or at least about 10 seconds, or at least about 30 seconds. In a preferred embodiment where the transition zone is part of an oxygenate-to-olefin riser-reactor system, the residence time is about 15 seconds.

The flow rate of steam, nitrogen, or other displacing gas out of the gas spargers can be characterized in terms of a superficial velocity. The superficial velocity of the gas emerging from the gas spargers can be determined by taking the total flow rate of gas and dividing it by the cross sectional area of the transition zone. Dimensionally, this corresponds to a flow rate for the gas in the direction perpendicular to the cross-section of the transition zone. In an embodiment, the superficial velocity of the displacing gas introduced by the gas spargers is about 0.03 m/sec or greater, or about 0.10 m/sec or greater, or about 0.15 m/sec or greater. In another embodiment where the transition zone is part of an oxygenate-to-olefin riser-reactor system, the superficial velocity of the gas introduced by the gas spargers is about 0.06 m/sec or greater, or about 0.09 m/sec or greater, or about 0.15 m/sec or greater.

Oxygenate to Olefin Reactions

An example of a reaction system that benefits from this invention is an oxygenate-to-olefin process, such as a methanol to olefin conversion reaction. Conventionally, oxygenate-to-olefin processes are carried out in a fluidized bed, fast fluidized bed, or riser reactor configuration where a fluid (gas) flow of a feedstock is passed through a bed of solid catalyst particles.

As used herein, the term "oxygenate" means one or more organic compound(s) containing at least one oxygen atom. For example, the oxygenate in the feedstock to an oxygenate-to-olefin process can be one or more alcohol(s), preferably aliphatic alcohol(s) where the aliphatic moiety of the alcohol (s) has from 1 to 20 carbon atoms, preferably from 1 to 10 carbon atoms, and most preferably from 1 to 4 carbon atoms. The alcohols include lower straight and branched chain aliphatic alcohols and their unsaturated counterparts, e.g., methanol, ethanol, n-propanol, isopropanol, methyl ethyl ether, dimethyl ether, diethyl ether, di-isopropyl ether, formaldehyde, dimethyl carbonate, dimethyl ketone, acetic acid, and the like, including mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock optionally contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

In an oxygenate to olefin reaction, a feed containing an oxygenate is contacted in a reaction zone of a reactor apparatus with a catalytically effective amount of a molecular sieve catalyst at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternatively, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

The conversion of oxygenates to produce light olefins may be carried out in a variety of large scale catalytic reactors, e.g., fluid bed reactors and concurrent riser reactors as described in Fluidization Engineering, D. Kunii and O. Levenspiel, Robert E. Krieger Publishing Co. NY, 1977. Additionally, countercurrent free fall reactors may be used in the conversion process. See, for example, U.S. Pat. No. 4,068,136 and Fluidization and Fluid-Particle Systems, pp. 48-59, F. A. Zenz and D. F. Othmer, Reinhold Publishing Corp., NY, 1960.

In one embodiment of this invention, the gas and solid particles are conducted through a gas-solids riser reactor at a weight hourly space velocity (WHSV) of from about 1 $hr^{-1}$ to about 5,000 $hr^{-1}$, preferably from about 5 $hr^{-1}$ to about 3,000 $hr^{-1}$, more preferably from about 10 $hr^{-1}$ to about 1,500 $hr^{-1}$, and most preferably from about 20 $hr^{-1}$ to about 1,000 $hr^{-1}$. In one preferred embodiment, the WHSV is greater than 25 $hr^{-1}$, and up to about 500 hr. In this invention, WHSV is defined as the total weight per hour of the gas flowing between reactor walls divided by the total weight of the solids flowing between the same segment of reactor walls. The WHSV is maintained at a level sufficient to keep the catalyst composition in a fluidized state within the riser reactor.

In a related embodiment, cyclones are used in conjunction with a riser reactor, and the gas and solid particles are conducted through the gas-solids riser reactor at a gas superficial velocity (GSV) at least about 1 meter per second (m/sec), preferably greater than about 2 m/sec, more preferably greater than about 3 m/sec, and most preferably greater than about 4 m/sec. The GSV should be sufficient to maintain the solids (i.e., catalyst) in a fluidized state in the riser, particularly in a fast fluidized state. In another related embodiment, the solids particles and gas are conducted through the riser reactor at a solids loading of at least about 0.1 lb/ft$^3$ (1.6 kg/m$^3$), or at least about 0.5 lb/ft$^3$ (8 kg/m$^3$), or at least about 1.0 lb/ft$^3$ (16 kg/m$^3$), or at least about 2.0 lb/ft$^3$ (32 kg/m$^3$), or at least about 4.0 lb/ft$^3$ (64 kg/m$^3$). Alternatively, the solids loading can be about 5 lb/ft$^3$ (80 kg/m$^3$) or less, or about 4.0 lb/ft$^3$ (64 kg/m$^3$) or less, or about 2.0 lb/ft$^3$ (32 kg/m$^3$) or less.

In one practical embodiment, the process is conducted as a fluidized bed process or high velocity fluidized bed process utilizing a riser reactor system, a regeneration system and a recovery system. In such a process the reactor system conveniently includes a fluid bed reactor system having a first reaction region comprising (preferably consisting of) a plurality of fast fluid or dense fluid beds in series or parallel and a second reaction region within at least one disengaging vessel, comprising two or more cyclones. In one embodiment, the fast fluid or dense fluid beds and disengaging vessel are contained within a single reactor vessel. Fresh feedstock, preferably containing one or more oxygenates, optionally with one or more diluent(s), is fed to the one or more fast fluid or dense fluid beds reactor(s) into which a molecular sieve catalyst composition (fresh, coked, or partially coked) is introduced. In another embodiment, prior to being introduced to the riser reactor(s), the molecular sieve catalyst composition is contacted with a liquid and/or vapor, preferably water and methanol, and a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process can be conducted over a wide range of temperatures, such as in the range of from about 200° C. to about 1000° C., for example, from about 250° C. to about 800° C., including from about 250° C. to about 750° C., conveniently from about 300° C. to about 650° C., typically from about 350° C. to about 600° C. and particularly from about 350° C. to about 550° C.

Similarly, the process can be conducted over a wide range of pressures including autogenous pressure. Typically the partial pressure of the feedstock exclusive of any diluent therein employed in the process is in the range of from about 0.1 kPa to about 5 MPa, such as from about 5 kPa to about 1 MPa, and conveniently from about 20 kPa to about 500 kPa.

In embodiments involving a riser reactor, the solids particles and gas are conducted through the gas-solids reactor at a solids to gas mass ratio of about 0.5:1 to about 75:1. Preferably, the solids particles and gas are conducted through the gas-solids reactor at a solids to gas mass ratio of about 8:1 to about 50:1, more preferably from about 10:1 to about 40:1.

During the conversion of a hydrocarbon feedstock, preferably a feedstock containing one or more oxygenates, the amount of olefin(s) produced based on the total weight of hydrocarbon produced is greater than about 50 weight percent, typically greater than about 60 weight percent, such as greater than about 70 weight percent, and preferably greater than about 75 weight percent. In one embodiment, the amount of ethylene and/or propylene produced based on the total weight of hydrocarbon product produced is greater than about 65 weight percent, such as greater than about 70 weight percent, for example, greater than about 75 weight percent, and preferably greater than about 78 weight percent. Typically, the amount ethylene produced in weight percent based on the total weight of hydrocarbon product produced, is greater than about 30 weight percent, such as greater than about 35 weight percent, for example, greater than about 40 weight percent. In addition, the amount of propylene produced in weight percent based on the total weight of hydrocarbon product produced is greater than about 20 weight percent, such as greater than about 25 weight percent, for example, greater than about 30 weight percent, and preferably greater than about 35 weight percent.

The feedstock entering the reactor system is preferably converted, partially or fully, in a reaction region into a gaseous effluent. In an embodiment, the reaction region is closely coupled to a plurality of separation devices, such as cyclone separators. In another embodiment, the gaseous effluent enters a disengaging vessel along with the coked catalyst composition. In such an embodiment, the disengaging vessel includes cyclone separators configured and/or operated according to the invention. In still another embodiment, the disengaging vessel also includes a stripping zone (which serves as the transition zone), typically in a lower portion of the disengaging vessel. In the stripping zone the coked catalyst composition is contacted with a stripping gas (which serves as the displacing gas), preferably one or a combination of steam, methane, carbon dioxide, carbon monoxide, hydrogen, or an inert gas such as argon, preferably steam, to recover adsorbed hydrocarbons from the coked catalyst composition. After exiting the separation devices and/or disengaging vessels, some or all of the catalyst can then be introduced to a regeneration system.

In an embodiment, at least a portion of the coked catalyst composition is withdrawn from one or more of the disengaging vessels and introduced to the regeneration system. The regeneration system comprises a regenerator where the coked catalyst composition is contacted with a regeneration medium, preferably a gas containing oxygen, under conventional regeneration conditions of temperature, pressure and residence time. In an embodiment, a gas-solids flow exiting a regenerator may be passed through cyclones configured according to the invention. Alternatively, at least a portion of the catalyst can be conducted to bypass the regeneration system. The catalyst bypassing the regenerator can be conducted to another desired portion of the reaction system, such as flowing the catalyst directly into a catalyst cooler or allowing the catalyst to rejoin a fluidized bed in the reactor. Preferably, the catalyst bypassing the regenerator is approximately evenly distributed into each of a plurality of standpipe entry locations.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example, from about 450° C. to about 750° C., and conveniently from about 550° C. to about 700° C. The regeneration pressure may be in the range of from about 15 psia (103 kPa) to about 500 psia (3448 kPa), such as from about 20 psia (138 kPa) to about 250 psia (1724 kPa), including from about 25 psia (172 kPa) to about 150 psia (1034 kPa), and conveniently from about 30 psia (207 kPa) to about 60 psia (414 kPa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler can be e.g., a heat exchanger that is located either internal or external to the regeneration system. Other methods for operating a regeneration system are in disclosed U.S. Pat. No. 6,290,916 (controlling moisture).

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In a preferred embodiment, the regenerated catalyst is returned to the transition zone in the separation vessel. This allows the regenerated catalyst to be combined with the non-regenerated catalyst for even distribution between each of the multiple standpipe entry locations. In another embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, pp. 336-337, 1997.

Coke levels on the catalyst composition can be measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example, from about 0.2 weight percent to about 5 weight percent, and conveniently from about 0.3 weight percent to about 2 weight percent based on the weight of the molecular sieve.

The gaseous reactor effluent is withdrawn from the disengaging system and is passed through a recovery system. Any recovery systems, techniques, and sequences can be used that are capable of separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture and other derivative processes such as aldehydes, ketones and ester manufacture, and other associated equipment, for example, various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, a wash tower often referred to as a caustic wash tower and/or quench tower, absorbers, adsorbers, membranes, ethylene (C2) splitter, propylene (C3) splitter and butene (C4) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a methanol to olefin ("MTO") process are passed through a purification system that removes low levels of by-products or contaminants. In an embodiment, prime olefin such as ethylene and propylene are separated from the oxygenate-to-olefin reaction system and polymerized to make polymers and copolymers of ethylene and/or propylene such as polyethylene and/or polypropylene.

Typically, in converting one or more oxygenates to olefin(s) having 2 or 3 carbon atoms, a minor amount of hydrocarbons, particularly olefin(s), having 4 or more carbon atoms is also produced. The amount of $C_4+$ hydrocarbons is normally less than 20 weight percent, such as less than 10 weight percent, for example, less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Alternative Riser Reactor Systems

In an embodiment, the oxygenate-to-olefin process is operated in a riser reactor system as illustrated in FIG. 1, 2A, and 2B, which uses multiple risers and standpipes. In another embodiment, the process is operated in a reaction system using a single riser reactor and a single standpipe, as shown in FIG. 4. Process conditions in the riser reactor, transition zone, standpipes, regenerator, catalyst cooler, product separation and upgrading stages, etc., can be similar to those in the previous embodiments.

As shown in FIG. 4, a riser reactor system for converting oxygenates to olefins comprises reactor-side components 300 and regenerator-side components 400. Oxygenate feedstock, at least some of which is in a vaporized form, is supplied through line 303 to a riser reactor 306, the reactor vessel including a reaction zone 309 comprising an inlet zone 304, that contains fluidizable molecular sieve catalyst particles provided from gas-displaced catalyst standpipe 324 and conduit 327 through circulation zone outlet 304 (element 304 serves as both the reaction zone inlet and circulation zone outlet).

Remaining with FIG. 4, an oxygenate conversion reaction takes place in and products including prime olefins are formed in reaction zone 309, and the fluidizable catalyst particles, now oxygenate-exposed, are carried into termination vessel 312 through reaction zone outlet 348 (element 348 is also the circulation zone inlet). Termination vessel 312 comprises a termination vessel volume 315, which is one element of the circulation zone, and is the first element of a disengaging zone that eventually leads to products leaving the reactor apparatus altogether through line 345. Termination vessel volume 315 is of substantially larger cross sectional area than the reaction zone, thus significantly slowing the gas superficial velocity ("GSV") in that termination space and allowing a large portion of the catalyst to settle downward with gravity and become largely separated from the oxygenate conversion products, and any diluent or unconverted oxygenate conversion feedstock that may be present. Another portion of the fluidizable catalyst particles are carried into a cyclone separator device 318, where catalyst is also largely separated from the oxygenate conversion products, and any diluent or unconverted oxygenate conversion feedstock that may be present, and falls into dipleg 321, where it is transferred into termination vessel volume 315. The catalyst in termination vessel volume 315 flows downward through transition zone inlet 351, marked with a dashed line at the demarcation of the cylindrical and conical sections, into transition zone 333.

Still with FIG. 4, a displacing gas is provided through line and sparger 336 to a location near the bottom of transition zone 333, causing the displacing gas to rise through transition zone 333, stripping the catalyst as it falls through transition zone 333. Some contacting devices, e.g., shed trays, are shown in transition zone 333 to facilitate catalyst stripping by the displacing gas. A majority of the gas-displaced catalyst exits transition zone 333 below displacing gas line and sparger 336 to enter and flow through circulation standpipe 324, and subsequently moves through line 327 where it joins regenerated catalyst coming from the regenerator 400 through line 412, and both types of catalyst are lifted against gravity through line 327 (via lift gas provided in line 403) to the reaction zone inlet 304 and to reaction zone 309. Optionally, a control valve 330 may be used on gas-displaced catalyst circulation standpipe 324. The remaining small portion of the gas-displaced catalyst from transition zone 333 may flow through regenerator entry standpipe 439 to catalyst regenerator vessel 401. Optionally, a control valve 442 may be used in regenerator entry standpipe 439. Regenerated catalyst may be returned to reaction zone 309 through the reaction zone inlet zone 304, in this example after having been cooled in catalyst cooler 406, passing through a line 409 in fluid communication with another line 412, and joining with the gas-displaced catalyst from line 324 in line 327. Optionally, a control valve 415 may be used in line 412. The large majority of oxygenate conversion products from the oxygenate conversion reaction in reaction zone 309, gas-displaced products from the transition zone 333, and unconverted oxygenate feedstock or diluents, if any, are removed from the reactor apparatus in line 345. Some small amount of such materials may be introduced into the regenerator 400 due to the imperfect nature of stripping in transition zone 333.

In the embodiment shown in FIG. 4, the circulation zone comprises elements 348 (as both the circulation zone inlet and reaction zone outlet), 315, 318, 351, 333, 336, 330, 324, 327, and 304 (as both the circulation zone outlet and reaction zone inlet). A determination of the residence time of catalyst within transition zone element 333 would be made, in order to develop the appropriate ratio including the residence time of catalyst in the reaction zone 309, which includes inlet zone 304. In general, the volume of the transition zone is that region in which the displacing gas superficial velocity is at least 0.03 m/s. For the embodiment illustrated in FIG. 4, the displacing gas superficial velocity provided by displacing gas from line and sparger 336 is 0.03 m/s in the cylindrical transition zone 333 directly above, and thus the volume of transition zone 333 is the volume encompassed between the sparger 336 and the transition zone inlet 351 (much above transition zone inlet 351, the increased area for flow in termination vessel volume 315 would quickly decrease the displacing gas superficial velocity).

Figure 5:
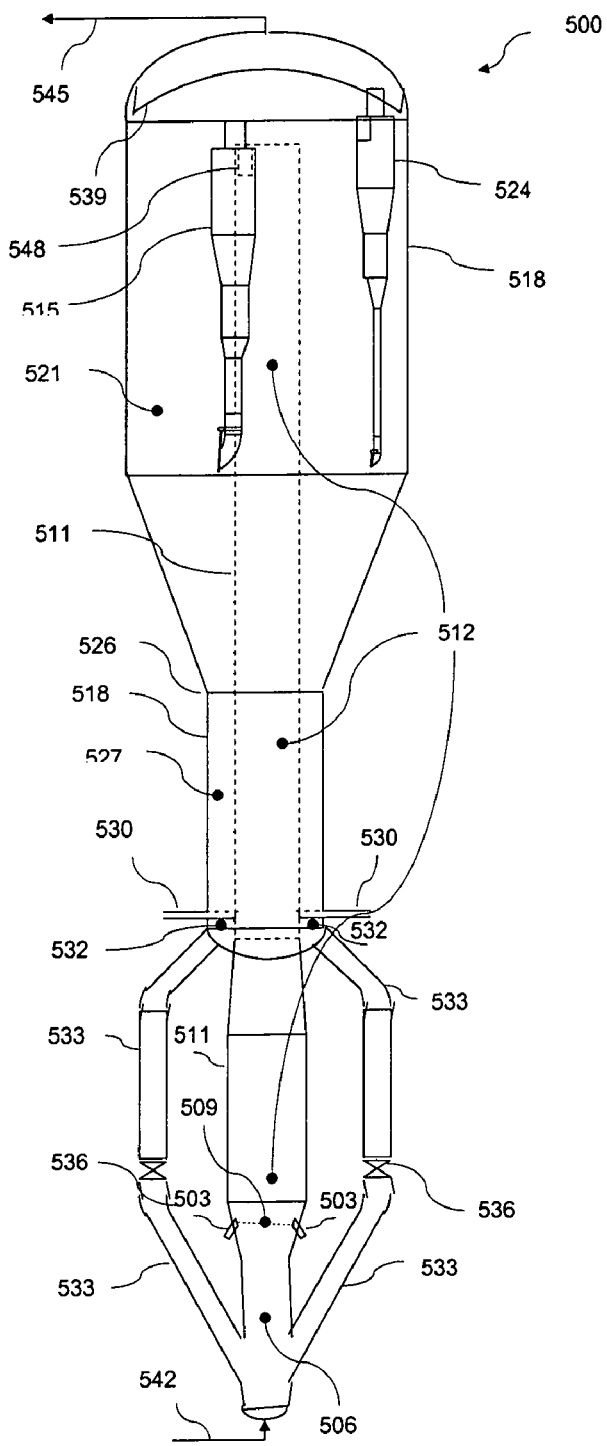
FIG. 5 schematically shows an apparatus according to an embodiment of the invention.

In another embodiment, shown in FIG. 5, the riser reactor zone is concentric with the separation and transition zones. Turning to the figure, oxygenate feedstock is supplied to oxygenate-to-olefin reaction system 500 through nozzles 503 and into a riser reactor vessel 511. The reactor vessel has a reaction zone 512 comprising a lower larger diameter cylinder, a frusto-conical section and a higher smaller diameter cylinder. Reaction zone 512 contains fluidizable, molecular sieve, gas-displaced catalyst particles provided from lower circulation zone 506 through circulation zone outlet 509 (element 509 also serves as the reaction zone inlet). Catalyst particles in lower circulation zone 506 are fluidized and lifted through circulation zone outlet 509 into reaction zone 512 by the introduction of a fluidization medium, such as steam, through line 542. In this example, the reaction zone inlet is determined to be the area just above where oxygenate feedstock is introduced, as that is the first place in the apparatus where contacting between the oxygenate feedstock and the gas-displaced catalyst can take place.

Continuing with FIG. 5, an oxygenate conversion reaction takes place in and products including prime olefins are formed in reaction zone 512, and the fluidizable particles, now oxygenate exposed, are carried into close coupled, primary cyclone separator 515 through reaction zone outlet 548 (element 548 is also the circulation zone inlet). In general, the reaction zone outlet is determined as the entrance to an element that works to separate catalyst from reaction product, which in this example is reaction zone outlet 548 as the entrance to primary cyclone separator 515.

Remaining with FIG. 5, oxygenate conversion product including light olefins, and any unconverted oxygenate feedstock and diluent that may be present, and a minor amount of catalyst exit the top of primary cyclone separator 515 into termination vessel volume 521 formed by termination vessel 518. The upper portion of termination vessel volume 521 is of substantially larger cross sectional area than the reaction zone, thus significantly slowing the GSV in that termination volume and allowing a large portion of any catalyst that may emanate from the top of primary cyclone 515 to settle downward with gravity and become largely separated from the oxygenate conversion products, and any diluent or unconverted oxygenate conversion feedstock that may be present. Reaction products, and any unconverted oxygenate feedstock and diluent that may be present in termination volume 521, and an even smaller amount of entrained catalyst enter secondary cyclone separator 524. Reaction products, and any unconverted oxygenate feedstock an diluent that may be present, and a very small amount of residual catalyst exit the top of secondary cyclone separator through plenum 539 and exit the reactor apparatus through line 545 for further processing. Alternatively, the top outlet of primary cyclone 515 may be close coupled to the inlet of secondary cyclone 524 so that very little reaction product and other attendant materials flow through termination vessel volume 521.

Still with FIG. 5, catalyst falls into the lower diplegs of primary cyclone separator 515 and secondary cyclone separator 524 into termination vessel volume 521, and along with any catalyst settling from elsewhere in termination vessel volume 521 flows downward through transition zone inlet 526, marked by a solid line at the demarcation of the cylindrical and conical sections of termination vessel 518, into annular transition zone 527, the annulus formed by the lower portion of termination vessel 518 and the higher smaller diameter portion of reactor vessel 511.

As shown in FIG. 5, a displacing gas is provided through lines and spargers 530 to a location near the bottom of transition zone 527, causing the displacing gas to rise through transition zone 527, stripping the catalyst as it falls through transition zone 527. Some contacting devices, e.g., shed trays, that may be present in transition zone 527 to facilitate stripping by the displacing gas, are not shown. A large portion of the gas-displaced catalyst from transition zone 527 falls into defluidization zone 532, and then enters circulation standpipes 533 and is moved to lower circulation zone 506 on its way back to the reaction zone. Optionally, control valves 536 may be used on gas-displaced catalyst circulation standpipes 533. In a separate embodiment, a small portion of the gas-displaced catalyst from transition zone 527 or elsewhere from the reactor apparatus 500 may flow to a regenerator, and regenerated catalyst from the regenerator may be returned to a desired location in reactor system 500.

In the embodiment shown in FIG. 5, the circulation zone comprises elements 548 (as the circulation zone inlet and reaction zone outlet), 515, 521, 524, 527, 530, 532, 533, 536, 506, 542 and 509 (as both the circulation zone outlet and reaction zone inlet). A determination of the residence time of catalyst within annular transition zone element 527 would be made, in order to develop the appropriate ratio of the residence time of catalyst in transition zone 527 to the residence time of catalyst in reaction zone 512. In general, the volume of the transition zone is that in which the gas superficial velocity of the displacing gas is at least 0.03 m/s. With reference to the embodiment of FIG. 5, it is assumed that the gas superficial velocity of the displacing gas from line and sparger 530 is 0.03 m/s in the annular transition zone 527 directly above, and thus the volume of transition zone 527 is the volume encompassed in the annular space between the lines and spargers 530 and the transition zone inlet 526 (much above transition zone inlet 526, the increased area for flow would quickly decrease the gas superficial velocity). Process conditions in the riser reactor, transition zone, standpipes, regenerator, catalyst cooler, product separation and upgrading stages, etc., can be similar to those in the previous embodiments.

The gas-solids separation techniques as described in the non-limiting embodiments above are particularly suited to large, commercial scale reaction systems. For example, the separation techniques of this invention are particularly suited to reaction systems that require a catalyst loading of at least about 1,000 kg of catalyst, based on total amount of catalyst located throughout the reaction system. In particular, the separation processes of this invention are particularly suited to reaction systems that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

Catalysts for Oxygenate to Olefin Conversion

As used herein, the term "catalyst" refers to a fluidizable material containing molecular sieve that is catalytically active for the conversion of oxygenate into olefin. The catalyst can be (i) a gas-displaced catalyst, (ii) an oxygenate-exposed catalyst, (iii) fresh catalyst (typically, catalyst that has neither been gas-displaced nor oxygenate exposed, in particular catalyst that has been recently manufactured) provided to or otherwise within the reactor apparatus, (iv) a regenerated catalyst provided to or otherwise within the reactor apparatus, or any combination thereof. In an embodiment, the catalyst contains a silicoaluminophosphate molecular sieve ("SAPOs") and/or mixtures of silicoaluminophosphate molecular sieves. Desired silicoaluminophosphate molecular sieves include "small" and "medium" pore molecular sieves. "Small pore" molecular sieves are defined as molecular sieves with pores having a diameter of less than about 5.0 Angstroms. "Medium pore" molecular sieves are defined as molecular sieves with pores having a diameter from about 5.0 to about 10.0 Angstroms.

SAPOs comprise a three-dimensional microporous crystal framework structure of $[SiO_2]$, $[AlO_2]$ and $[PO_2]$ tetrahedral units. The way Si is incorporated into the structure can be determined by 29Si MAS NMR. See Blackwell and Patton, J. Phys. Chem., 92, 3965 (1988). The desired SAPO molecular sieves will exhibit one or more peaks in the 29Si MAS NMR, with a chemical shift [(Si)] in the range of –88 to –96 ppm and with a combined peak area in that range of at least 20% of the total peak area of all peaks with a chemical shift [(Si)] in the range of –88 ppm to –115 ppm, where the [(Si)] chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5-15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

In various embodiments, the SAPO molecular sieve may include a $Si/Al_2$ ratio of at least 0.10 and no greater than 0.32, or at least 0.12 and no greater than 0.30, or at least 0.14 and no greater than 0.28, or at least 0.15 and no greater than 0.26. In general, for a SAPO, higher $Si/Al_2$ ratios provide inherently higher activity to convert methanol. However, as the invention is directed to providing and maintaining high catalyst activity, a $Si/Al_2$ ratio of over 0.32 is likely to produce an excessive apparent catalyst activity that will have a disadvantageous yield of byproducts. Further, in general, for a SAPO, lower $Si/Al_2$ ratios provide certain good attributes, such as low coke yield, but also can provide under certain conditions a lower ratio of ethylene to propylene.

The catalyst may further contain, in certain proportions, binders, fillers, or other material to provide better catalytic performance, attrition resistance, regenerability, and other desired properties. The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like. These binder and filler materials are generally catalytically inert, and include but are not limited to compositions such as kaolin and other clays, various forms of rare earth metals, metal oxides, other non-zeolite catalyst components, alumina or alumina sol, titania, zirconia, magnesia, thoria, beryllia, quartz, silica or silica or silica sol, and mixtures thereof. Preferred proportions of SAPO in the catalyst are formulations containing at least 35, alternately at least 40. In concert with the objective of the invention to practically maximize reactor productivity with good light olefin yield, particularly advantageous proportions of SAPO in the catalyst are formulations containing least 45, alternately at least 50, alternately at least 55, alternately at least 60 and alternately at least 65 wt. % SAPO.

In other embodiments, the catalyst can include, in addition to a SAPO and/or binders and fillers, one or more other useful zeolitic molecular sieves (generally termed aluminosilicates, which typically include silicon and aluminum but do not include phosphorous in the framework) including, but not limited to, mordenite, chabazite, erionite, ZSM-5, ZSM-34, ZSM-48 and mixtures thereof. Methods of making these zeolite molecular sieves are known in the art and need not be discussed here. Structural types of small pore aluminosilicate molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore aluminosilicate molecular sieves that are suitable for use in this invention include MFI, MEL, MTW, EUO, MTT, HEU, FER, AFO, AEL, TON, and substituted forms thereof. These small and medium pore zeolites are described in greater detail in the Atlas of Zeolite Structural Types, W. M. Meier and D. H. Olsen, Butterworth Heineman, 3rd ed., 1997, the detailed description of which is explicitly incorporated herein by reference.

In an embodiment, the oxygenate-to-olefin catalyst has the following preferred size distribution:

(i) 95 wt. % of the catalyst particles have an average size less than 125 micrometers, (ii) 90 wt. % of the catalyst particles have an average size less than 110 micrometers, (iii) 80 wt. % of the catalyst particles have an average size less than 96 micrometers, (iv) 70 wt. % of the catalyst particles have an average size less than 88 micrometers, (v) 60 wt. % of the catalyst particles have an average size less than 83 micrometers, (vi) 50 wt. % of the catalyst particles have an average size less than 78 micrometers, (vii) 40 wt. % of the catalyst particles have an average size less than 74 micrometers, (viii) 30 wt. % of the catalyst particles have an average size less than 69 micrometers, (ix) 20 wt. % of the catalyst particles have an average size less than 65 micrometers, (x) 10 wt. % of the catalyst particles have an average size less than 59 micrometers, (xi) 5 wt. % of the catalyst particles have an average size less than 54 micrometers, (xii) 1 wt. % of the catalyst particles have an average size less than 46 micrometers, and (xiii) no more than 0.5 wt. % of the catalyst particles have an average size less than 44 micrometers;

the percents being based on the total weight of the catalyst particles.

Exemplary Embodiments

Aspects of the invention were implemented and tested in a cold flow test apparatus at near atmospheric pressure and ambient temperature using an oxygenate-to-olefin conversion catalyst in fluidized form. In the test apparatus, five 20 cm risers were joined together in a system having a single separation vessel with a roughly 1 meter diameter. Air was used as the sparging and transport gas. Flows exiting the risers entered the separation vessel via a cyclone separator. The higher density flows exiting diplegs of a cyclone separator passed down into a transition zone containing 6 levels of baffles or sheds. The 6 levels of baffles or sheds were organized into 3 pairs of levels, with the sheds in each pair rotated by 90 degrees relative to the sheds in an adjacent pair of levels. Within a pair, the sheds were positioned so that an opening in one level of the pair corresponded to a shed location in the other level of the pair.

Figure 6:
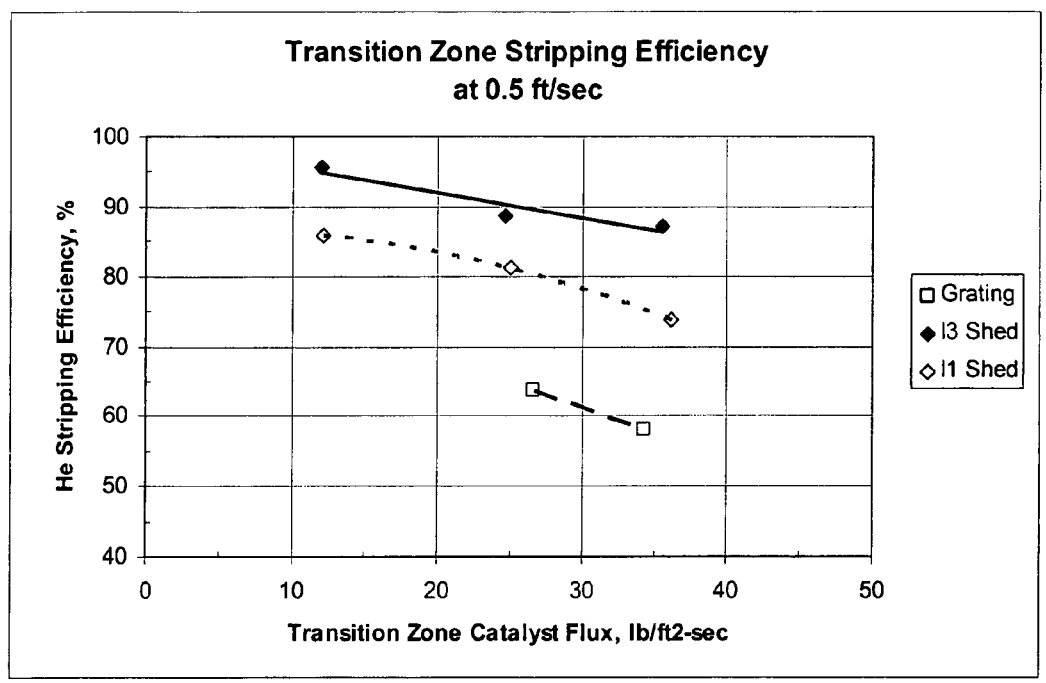
FIG. 6 shows results of operation of an apparatus according to an embodiment of the invention.

To test the ability of the gas spargers and baffles for removing gases adhered to (or entrained in) the catalyst, helium was injected into the gas-solids flow as the flow exited the diplegs of the cyclone separators. The removal efficiency was determined by measuring the amount of helium remaining in the solids flow as the solids flow entered the standpipe entry location, as compared to the amount of helium in the solids flow at the top of the bed. FIG. 6 shows the impact of various types of baffles or sheds on the removal efficiency of the helium from the gas-solids flow. The types of baffles used are noted in the figure. The grating baffles are similar to a subway grating consisting of multiple narrow metal slats or strips placed perpendicular to the flow and spaced about every inch with one inch openings between each strip. The I1 sheds represent inverted v-shaped structures. The I3 sheds are similar to the I1 sheds, but additionally have a vertical surface at each of the lower edges of the v-shaped structure and are perforated with holes to allow gas to pass through the shed. Multiple rows of baffles were used in all of the cases shown in FIG. 6. The superficial velocity of air injected by the gas spargers in all cases shown is 0.5 ft/sec (0.15 m/sec).

In FIG. 6, the stripping efficiency of the combination of baffles and stripping gas from the gas spargers is shown relative to the flux of catalyst passing through the transition zone. Stripping efficiency is defined as the percentage of the vapor component entering the top of the transition zone that is displaced and does not enter the standpipe at the bottom of the transition zone. While all of the baffles show some effectiveness in separating helium from the solids, the I3 sheds have the highest percentage removal of the injected helium from the solids flow. The removal efficiency declines as the flux within the transition zone increases (which corresponds to an increase in the flux in the standpipes as well). However, the removal efficiency does not decline to the extent that would be expected if FCC molecular sieve catalyst (e.g. USY) were used. In other words, it would be desirable to operate FCC transition zones (typically the stripper zone) at transition zone catalyst fluxes of 100 kg/m$^2$*sec or more, but this is not generally possible without incurring a significant loss in stripping efficiency. While not wishing to be bound by any theory or model, it is believed that such high transition zone fluxes (above about 100 kg/m$^2$*sec, or above about 125 kg/m$^2$*sec, or even above about 150 kg/m$^2$*sec) are possible in an oxygenate-to-olefin ("OTO") reaction system by virtue of that process's catalyst, feed, and product characteristics. Particularly when the preferred catalyst size distribution is used, it is believed that the size of the gas bubbles formed in the OTO transition zone are significantly larger than the average gas bubble size that forms in FCC strippers. This effect results in a significant increase in the amount of displacing gas moving upward (countercurrent to catalyst flow) in the transition zone at a given catalyst flux, which in turn leads to increased catalyst stripping efficiency.

It is also believed that it is intrinsically easier to strip an OTO molecular sieve catalyst used in and OTO reaction system compared to an FCC catalyst used in gas oil or heavy oil cracking because the OTO feed and reaction product molecules are lighter and easier to displace from the OTO catalyst than FCC feed and reaction products from an FCC catalyst.

Figure 7:
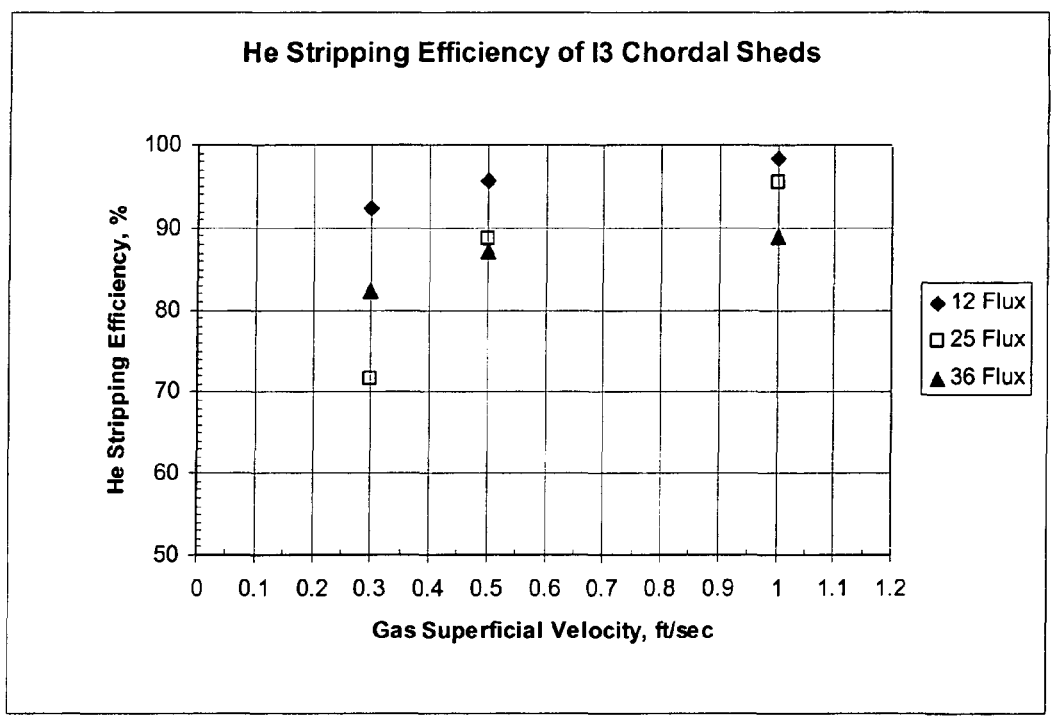
FIG. 7 shows results of operation of an apparatus according to an embodiment of the invention.

FIG. 7 shows the effect of varying the superficial velocity of the sparging gas on the removal efficiency of the helium from the solids flow. The superficial velocity of the sparging gas corresponds to the total flow rate of the gas divided by the cross sectional area of the separation vessel. In these measurements, the I3 style sheds were used. As shown in FIG. 7, the removal efficiency approaches 90% for all transition zone solid flux values when the sparging gas superficial velocity is 0.5 ft/sec (0.15 m/sec) or larger.

In various embodiments, the stripping or displacing efficiency of the stripping gas can be at least 50%, or at least 70%, or at least 90%. Alternatively, the stripping efficiency can be 99.9% or less, or 95% or less.

Figure 8:
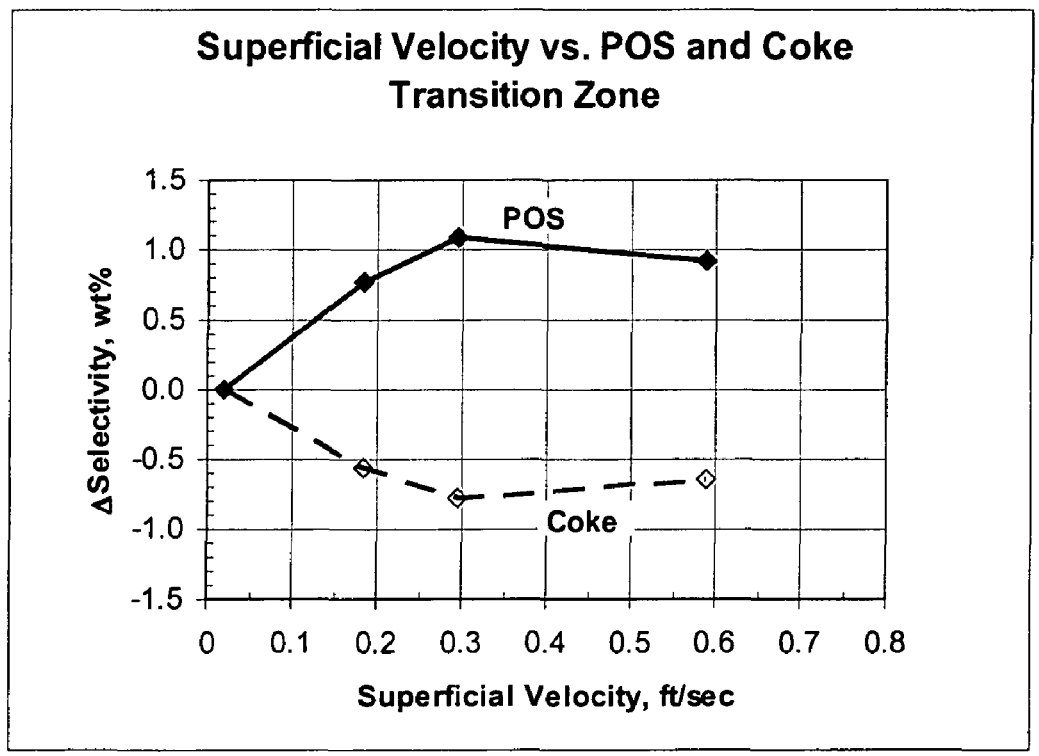
FIG. 8 shows results of operation of an apparatus according to an embodiment of the invention.

FIG. 8 shows the effect of incorporating an embodiment of the invention into a pilot plant for performing a methanol-to-olefin conversion reaction. In FIG. 8, gas spargers were incorporated into the separation vessel for the pilot plant, but no additional baffles were used. FIG. 8 shows the impact on prime olefin selectivity (POS) and coke selectivity from that in a baseline pilot experiment. Selectivity is defined as the weight of the product component divided by the weight of the total product excluding water on a percentage basis. In the baseline experiment, only a minimal flow of sparging gas was conducted through the gas inlets to prevent clogging of the gas inlets by catalyst particles. Increasing the superficial velocity of the sparging gas to 0.2 or 0.3 ft/sec (0.06 or 0.09 m/sec) provided a noticeable increase in the POS while also suppressing coke selectivity. Superficial velocities above 0.3 ft/sec (0.09 m/sec), however, did not appear to provide further improvement in the POS and did not further suppress coke selectivity.

In various embodiments, flowing a stripping gas through the transition zone can produce an increase in POS of at least 0.1%, or at least 0.5%, or at least 1.0%. Alternatively, flowing a stripping gas through the transition zone can produce an increase in POS of 5% or less, or 2% or less. In other embodiments, flowing a stripping gas through the transition zone can produce a decrease in coke selectivity of at least 0.1%, or at least 0.5%, or at least 1.0%. Alternatively, flowing a stripping gas through the transition zone can produce a decrease in coke selectivity of 5% or less, or 2% or less.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for separating flowing solids comprising:
    separating from a gas-solids flow a higher density flow comprising a majority of the solids contained in the gas-solids flow;
    conducting all of the solids from the higher density flow through a transition zone at a transition zone solids flux of at least about 100 kg/m²-sec in the presence of a displacing gas flowing counter-currently with respect to average solids flow; and then
    conducting the displaced solids away from the transition zone through the solids outlet and into one or more standpipes coupled to solids outlets and separated from at least one displacing gas inlet by a distance dependent on the cross sectional area of the standpipes at the entry location and the desired solid catalyst flux through the standpipes and reaction system.

2. The method of claim 1, wherein the transition zone comprises
    (a) a solids inlet,
    (b) a solids outlet having an area A, and
    (c) a displacing gas inlet, located a vertical distance D from the solids outlet wherein D and A are related by the function $D=KA^{0.5}$ with K ranging from about 0.3 to about 1.5.

3. The method of claim 2, wherein the transition zone comprises at least one baffle layer, and wherein the displacing gas inlets are either (i) proximate to the baffle layer closest to the solids outlet or (ii) between the solids outlet and the baffle layer closest to the solids outlet.

4. The method of claim 2, wherein the transition zone comprises at least one pair of baffle layers, and wherein an orientation of one layer of the pair of baffle layers is rotated by about 90 degrees relative to the second layer of the pair of baffle layers.

5. The method of claim 1, wherein the displacing gas within the transition zone has a gas superficial velocity of at least about 0.03 msec.

6. The method of claim 1, wherein (i) the solids comprise catalyst particles containing molecular sieve with hydrocarbon and/or oxygenated hydrocarbon thereon or therein, (ii) wherein the hydrocarbon and/or oxygenated hydrocarbon is displaced from the catalyst particles in the transition zone at a displacing efficiency of at least about 50%.

7. The method of claim 6, wherein the displacing gas is steam, and the steam has a gas superficial velocity in the transition zone of at least about 0.09 meters per second.

8. The method of claim 7, wherein
    (i) the catalyst particles have an average flux through the transition zone ranging from about 125 kg/m²-sec to about 488 kg/m²-sec,
    (ii) the catalyst particles have an average catalyst residence time in the transition zones ranging from about 5 seconds to about 10 minutes, and
    (iii) the catalyst particles in the transition zone have an average catalyst density gradient of about 525 kg/m³-m or less,
    (iv) at least about 95 wt. % of the catalyst particles in the transition zone have an average particles size of about 125 micrometers or less based on the total weight of catalyst particles in the transition zone,
    (v) D is at least about 250 mm and A is at least about $2.7 \times 10^4$ square millimeters, and
    (vi) K ranges from about 0.8 to about 1.1.

9. The method of claim 7 where the transition zone comprises a plurality of solids outlets, each of the solids outlets having a cross sectional area A, and wherein a portion of the catalyst is conducted away from the transition zone through each of the plurality solids outlets into a plurality of standpipes, each of the standpipes being of even cross sectional area with the solids outlets and being directly connected to one of the solids outlets.

10. The method of claim 9, wherein at least a portion of the catalyst in the transition zone is in a fluidized bed, the fluidized bed having a density gradient of about 53 kg/m³-m or less, and wherein there is a volume fraction of bubbles at the catalyst outlet of at least about 0.00005.

11. The method of claim 7 wherein the catalyst particles contain SAPO 34 molecular sieve, the catalyst particles being characterized by a size distribution of
    (i) about 95 wt. % of the catalyst particles have an average size less than about 125 micrometers,
    (ii) about 90 wt. % of the catalyst particles have an average size less than about 110 micrometers,
    (iii) about 80 wt. % of the catalyst particles have an average size less than about 96 micrometers,
    (iv) about 70 wt. % of the catalyst particles have an average size less than about 88 micrometers,
    (v) about 60 wt. % of the catalyst particles have an average size less than about 83 micrometers,
    (vi) about 50 wt. % of the catalyst particles have an average size less than about 78 micrometers,
    (vii) about 40 wt. % of the catalyst particles have an average size less than about 74 micrometers,
    (viii) about 30 wt. % of the catalyst particles have an average size less than about 69 micrometers,
    (ix) about 20 wt. % of the catalyst particles have an average size less than about 65 micrometers,
    (x) about 10 wt. % of the catalyst particles have an average size less than about 59 micrometers,
    (xi) about 5 wt. % of the catalyst particles have an average size less than about 54 micrometers,
    (xii) about 1 wt. % of the catalyst particles have an average size less than about 46 micrometers, and (xiii) no more than about 0.5 wt. % of the catalyst particles have an average size less than about 44 micrometers;
the wt, percents being based on the total weight of the catalyst particles.

12. The method of claim 1 wherein the transition zone comprises a plurality of solids outlets, each solids outlet having a cross sectional area A, with each of the solids outlets being connected to one of a plurality of standpipes, with each standpipe having a cross sectional area equal to about A.

13. A method for making olefins, comprising
contacting a feed containing at least one oxygenate with a SAPO-containing catalyst in a riser reactor,
separating the catalyst particles from the olefins and conducting at least a portion of the catalyst to a transition zone having a catalyst flux of at least about 100 kg/m$^2$-sec in the presence of a displacing gas flowing counter-currently with respect to average catalyst flow;
displacing at least some of the oxygenate and/or olefin from the catalyst in the transition zone, and then
conducting at least a portion of the displaced catalyst through a solids outlet and into one or more standpipes coupled to solids outlets and separated from at least one displacing gas inlet by a distance dependent on the cross sectional area of the standpipes at the entry location and the desired solid catalyst flux through the standpipes and reaction system to the riser reactor;
wherein the transition zone comprises
(a) a catalyst inlet,
(b) the solids outlet having an area A, and
(c) the displacing gas inlet, located a vertical distance D from the catalyst outlet wherein D and A are related by the function $D=KA^{0.5}$ with K ranging from about 0.3 to about 1.5.

14. The method of claim 13 wherein the catalyst is in the form of catalyst particles containing SAPO molecular sieve, the catalyst particles being characterized by a size distribution of
(i) about 95 wt. % of the catalyst particles have an average size less than about 125 micrometers,
(ii) about 90 wt. % of the catalyst particles have an average size less than about 110 micrometers,
(iii) about 80 wt. % of the catalyst particles have an average size less than about 96 micrometers,
(iv) about 70 wt. % of the catalyst particles have an average size less than about 88 micrometers,
(v) about 60 wt. % of the catalyst particles have an average size less than about 83 micrometers,
(vi) about 50 wt. % of the catalyst particles have an average size less than about 78 micrometers,
(vii) about 40 wt. % of the catalyst particles have an average size less than about 74 micrometers,
(viii) about 30 wt. % of the catalyst particles have an average size less than about 69 micrometers,
(ix) about 20 wt. % of the catalyst particles have an average size less than about 65 micrometers,
(x) about 10 wt. % of the catalyst particles have an average size less than about 59 micrometers,
(xi) about 5 wt. % of the catalyst particles have an average size less than about 54 micrometers,
(xii) about 1 wt. % of the catalyst particles have an average size less than about 46 micrometers, and
(xiii) no more than about 0.5 wt. % of the catalyst particles have an average size less than about 44 micrometers;
the wt, percents being based on the total weight of the catalyst particles.

15. The method of claim 14, wherein (i) the catalyst particles have an average flux through the transition zone ranging from about 125 kg/m$^2$-sec to about 488 kg/m$^2$-sec,
(ii) the catalyst particles have an average catalyst residence time in the transition zones ranging from about 5 seconds to about 10 minutes, and
(iii) the catalyst particles in the transition zone have an average catalyst density gradient of about 525 kg/m$^3$-m or less,
(iv) at least about 95 wt. % of the catalyst particles in the transition zone have an average particles size of about 125 micrometers or less based on the total weight of catalyst particles in the transition zone;
(v) D is at least about 250 mm and A is at least about $2.7 \times 10^4$ square millimeters,
(vi) K ranges from about 0.8 to about 1.1; and
(vii) the displacing gas is steam.

16. The method of claim 15 wherein the transition zone comprises a plurality of catalyst outlets, each of the catalyst outlets having a cross sectional area equal to A, and wherein a portion of the catalyst is conducted away from the transition zone through each of the plurality catalyst outlets into a plurality of standpipes and then to the riser reactor, each of the standpipes being of even cross sectional area with the catalyst outlets, and wherein the catalyst flux in the standpipes ranges from about 488 kg/m$^2$ sec to about 1710 kg/m$^2$ sec.

17. A method for separating flowing catalyst particles comprising:
separating from a gas-catalyst flow a higher density flow comprising a majority of the catalyst particles contained in the gas-catalyst flow;
conducting all of the catalyst particles from the higher density flow through a transition zone at a transition zone catalyst flux ranging from about 125 kg/m$^2$-sec to about 488 kg/m$^2$-sec in the presence of steam, with the steam flowing counter-currently with respect to average catalyst particle flow at a gas superficial velocity of at least about 0.09 meters per second, with the catalyst particles in the transition zone have an average catalyst density gradient of about 525 kg/m$^3$-m or less; with the catalyst particles having an average catalyst residence time in the transition zones ranging from about 5 seconds to about 10 minutes, with at least about 95 wt. % of the catalyst particles in the transition zone having an average particles size of about 125 micrometers or less based on the total weight of catalyst particles in the transition zone; and then
conducting the displaced catalyst particles away from the transition zone through a solids outlet and into one or more standpipes coupled to solids outlets and separated from at least one displacing gas inlet by a distance dependent on the cross sectional area of the standpipes at the entry location and the desired solid catalyst flux through the standpipes and reaction system; wherein the transition zone comprises
(a) a solids inlet,
(b) the solids outlet having an area A,
(c) a baffle layer located between the solids inlet and the solids outlet,
(d) the displacing gas inlet, located a distance D from the solids outlet and either (i) proximate to the baffle layer or (ii) between the solids outlet and the baffle layer; wherein D and A are related by the function $D=KA^{0.5}$ wherein K ranges from about 0.8 to 1.5; D is at least about 250 mm; and A is at least about $2.7 \times 10^4$ square millimeters.

18. A method for separating solids from a gas-solids flow comprising:

producing a gas-solids flow by performing an oxygenate to olefin conversion reaction in a reactor;

separating from the gas-solids flow a higher density flow comprising a majority of the solids contained in the gas-solids flow;

conducting all of the solids from each higher density flow to a transition zone;

conducting the solids from the higher density flow through a transition zone at a transition zone solids flux of at least about 100 kg/m²-sec in the presence of a displacing gas flowing counter-currently with respect to average solids flow; and then conducting the solids away from the transition zone through a plurality of solids outlets, with each solids outlet being connected to at least one of a plurality of standpipes coupled to solids outlets and separated from at least one displacing gas inlet by a distance dependent on the cross sectional area of the standpipes at the ent location and the desired solid catalyst flux through the standpipes and reaction system to the olefin conversion reactor; the transition zone comprising (a) a solids inlet, (b) the solids outlet having an area A, (c) a baffle layer located between the solids inlet and the solids outlet, (d) the displacing gas inlet, located a distance D from the solids outlet and either (i) proximate to the baffle layer or (ii) between the solids outlet and the baffle layer; wherein D and A are related by the function $D=KA^{0.5}$ with K ranging from about 0.3 to about 1.5.

19. The method of claim 18, wherein the transition zone comprises a plurality of baffle layers, and wherein the displacing gas inlets are either (i) proximate to the baffle layer closest to the solids outlet or (ii) between the solids outlet and the baffle layer closest to the solids outlet.

20. The method of claim 18, wherein the transition zone comprises at least one pair of baffle layers, and wherein an orientation of one layer of the pair of baffle layers is rotated by about 90 degrees relative to the second layer of the pair of baffle layers.

21. The method of claim 18, wherein a superficial velocity of the displacing gas within the transition zone is about 0.03 msec or greater.

22. The method of claim 18, wherein (i) the solids comprise catalyst particles containing molecular sieve with hydrocarbon and/or oxygenated hydrocarbon thereon or therein, (ii) wherein the hydrocarbon and/or oxygenated hydrocarbon is stripped from the catalyst particles in the transition zone at a stripping efficiency of at least about 50%.

23. The method of claim 22, wherein the displacing gas is steam, and the steam has a gas superficial velocity in the transition zone of at least 0.09 meters per second.

24. The method of claim 23, wherein within the transition zone (i) the average catalyst flux ranges from about 125 kg/m²-sec to about 488 kg/m²-sec, (ii) the average catalyst residence time ranges from about 5 seconds to about 10 minutes, and (iii) the average catalyst density gradient is about 525 kg/m³-m or less, and (iv) D is at least about 250 mm and A is at least about $2.7 \times 10^4$ square millimeters.

25. The method of claim 24 wherein the catalyst is conducted away from the transition zone through the solids outlet and into a standpipe having a standpipe cross-sectional area no greater than A, and then from the standpipe to the olefin conversion reactor.

26. The method of claim 25 wherein the transition zone comprises a plurality of solids outlets, each of the solids outlets having a cross sectional area equal to A, and wherein a portion of the catalyst is conducted away from the transition zone through each of the plurality solids outlets into a plurality of standpipes to the olefin conversion reactor, each of the standpipes being of even cross sectional area with the solids outlets and having (i) an upstream end directly connected to one of the solids outlets and (ii) a downstream end.

27. The method of claim 26 wherein the olefin conversion reactor comprises a plurality of riser reactors, where the catalyst is conducted from the downstream end of each standpipe into at least one riser of the riser reactor.

28. The method of claim 25, wherein at least a portion of the catalyst in the transition zone is in a fluidized bed, the fluidized bed having a density gradient of about 53 kg/m³-m or less, and wherein there is a volume fraction of bubbles at the catalyst outlet of at least about 0.00005.

29. The method of claim 22 wherein the catalyst comprises SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

30. The method of claim 18, further comprising separating from the gas-solids flow a product comprising olefin and then polymerizing at least a portion of the olefin to make at least one polyolefin.

* * * * *